United States Patent
Gholoobi et al.

(10) Patent No.: US 11,560,564 B2
(45) Date of Patent: Jan. 24, 2023

(54) APTAMERS FOR TARGETING HPV16-POSITIVE TUMOR CELLS

(71) Applicants: Aida Gholoobi, Mashhad (IR); Zahra Meshkat, Mashhad (IR); Khalil Abnous, Mashhad (IR); Majid Ghayour Mobarhan, Mashhad (IR)

(72) Inventors: Aida Gholoobi, Mashhad (IR); Zahra Meshkat, Mashhad (IR); Khalil Abnous, Mashhad (IR); Majid Ghayour Mobarhan, Mashhad (IR)

( * ) Notice: Subject to any disclaimer, the term of this patent is extended or adjusted under 35 U.S.C. 154(b) by 219 days.

(21) Appl. No.: 17/128,286

(22) Filed: Dec. 21, 2020

(65) Prior Publication Data

US 2021/0115448 A1    Apr. 22, 2021

Related U.S. Application Data

(60) Provisional application No. 62/952,264, filed on Dec. 22, 2019.

(51) Int. Cl.
| | |
|---|---|
| *C12N 15/11* | (2006.01) |
| *C12N 15/113* | (2010.01) |
| *C12Q 1/6886* | (2018.01) |

(52) U.S. Cl.
CPC ........ *C12N 15/1131* (2013.01); *C12Q 1/6886* (2013.01); *C12N 2310/16* (2013.01); *C12N 2310/3517* (2013.01); *C12Q 2563/149* (2013.01); *C12Q 2563/155* (2013.01); *C12Q 2563/173* (2013.01)

(58) Field of Classification Search
None
See application file for complete search history.

(56) References Cited

PUBLICATIONS

Wang et al., In vitro selection of DNA aptamer by cell-SELEX as a molecular probe for cervical cancer recognition and imaging, Journal of Molecular Evolution, 2019, 87: 72-82 (Year: 2019).*

* cited by examiner

*Primary Examiner* — Ekaterina Poliakova-Georgantas
(74) *Attorney, Agent, or Firm* — Bajwa IP Law Firm; Haris Zaheer Bajwa

(57) ABSTRACT

A composition for binding to human papillomavirus type 16 (HPV16)-positive tumor cells, the composition including a DNA aptamer. The DNA aptamer includes one of SEQ ID NO: 1 and SEQ ID NO: 2.

20 Claims, 22 Drawing Sheets
Specification includes a Sequence Listing.

SEQUENCE LISTING

```
<160> NUMBER OF SEQ ID NOS: 5

<210> SEQ ID NO 1
<211> LENGTH: 80
<212> TYPE: DNA
<213> ORGANISM: Artificial Sequence
<220> FEATURE:
<223> OTHER INFORMATION: DNA aptamer

<400> SEQUENCE: 1
gctgtgtgac tcctgcaaca acccgtatag ggccacgtga aattttaact tgtctgaacc      60
ggcagctgta tcttgtctcc                                                 80

<210> SEQ ID NO 2
<211> LENGTH: 83
<212> TYPE: DNA
<213> ORGANISM: Artificial Sequence
<220> FEATURE:
<223> OTHER INFORMATION: DNA aptamer

<400> SEQUENCE: 2
gctgtgtgac tcctgcaatt ggctggccca actaggttag gtgtgatctt atcaccgaga      60
gcttgcagct gtatcttgtc tcc                                             83

<210> SEQ ID NO 3
<211> LENGTH: 80
<212> TYPE: DNA
```

```
<213> ORGANISM: Artificial Sequence
<220> FEATURE:
<223> OTHER INFORMATION: Library sequence
<220> FEATURE:
<221> NAME/KEY: misc_feature
<222> LOCATION: (19)..(61)
<223> OTHER INFORMATION: n is a, t, c, or g

<400> SEQUENCE: 3
gctgtgtgac tcctgcaann nnnnnnnnnn nnnnnnnnnn nnnnnnnnnn nnnnnnnnnn    60
ngcagctgta tcttgtctcc                                                80

<210> SEQ ID NO 4
<211> LENGTH: 18
<212> TYPE: DNA
<213> ORGANISM: Artificial Sequence
<220> FEATURE:
<223> OTHER INFORMATION: Forward primer

<400> SEQUENCE: 4
gctgtgtgac tcctgcaa                                                  18

<210> SEQ ID NO 5
<211> LENGTH: 19
<212> TYPE: DNA
<213> ORGANISM: Artificial Sequence
<220> FEATURE:
<223> OTHER INFORMATION: Reverse primer

<400> SEQUENCE: 5
ggagacaaga tacagctgc                                                 19
```

APTAMERS FOR TARGETING HPV16-POSITIVE TUMOR CELLS

CROSS-REFERENCE TO RELATED APPLICATION

This application claims the benefit of priority from U.S. Provisional Patent Application Ser. No. 62/952,264, filed on Dec. 22, 2019, and entitled "SELECTION OF DNA APTAMER TARGETING CERVICAL CANCER CELLS," which is incorporated herein by reference in its entirety.

TECHNICAL FIELD

The present disclosure generally relates to targeting HPV-positive tumor cells, particularly to targeting HPV16-positive tumor cells, and more particularly to DNA aptamers against HPV16-positive tumor cells.

BACKGROUND

Human papillomavirus (HPV) may cause almost all cervical cancers and may additionally cause some anogenital, and head and neck cancers. High-risk types of HPV may change normal cells to abnormal cells, which may lead to cancer if not treated. HPV16 is the most common high-risk type of HPV, which may cause uterine cervical changes without any noticeable symptoms. Most of the cancers may be prevented with early detection followed by treatment; thus, regular HPV tests for high-risk types are suggested for primary screening of cancers.

Despite significant improvements in the early treatment of cervical cancer such as surgery, radiation therapy, and chemotherapy, serious complications such as resistance to chemotherapy drugs and metastasis remain critical clinical challenges. Generally, current cancer treatments face many limitations, such as inability to cross biological barriers, inappropriate drug delivery, poor drug distribution, ineffective against metastasis, presence of drug-resistant cancers, and lack of practical approaches in monitoring the treatment. Nowadays, developing targeted substances or anti-cancer drugs that have been created for molecular diagnosis or treatment of cancers have helped significantly in improving diagnosis and treatment of these cancers.

Aptamers, which are short single-stranded oligonucleotides of DNA, RNA, or specific proteins, may be suitable candidates for targeting therapeutic and diagnostic compounds due to their high specificity and affinity. Targets of aptamers may vary from a single molecule to a complex target and even a whole organism. The basis for target identification by the aptamers is their tertiary structures. Compared to other ligands, oligonucleotide aptamers have distinct advantages, such as cost-effective production, low immunogenicity, high affinity comparable to monoclonal antibodies, and an ability to penetrate solid tumors.

Hence, there is a need for targeted compositions containing specific aptamers with high affinity against HPV16-positive tumor cells for early detection of pre-cancerous and cancerous cells. Also, there is a need to target HPV16-positive tumor cells using specific aptamers for in-vivo and in-vitro diagnostic and therapeutic applications.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary composition for binding to human papillomavirus type 16 (HPV16)-positive tumor cells. In an exemplary embodiment, the composition may include an exemplary DNA aptamer. In an exemplary embodiment, an exemplary DNA aptamer may include one of SEQ ID NO: 1 and SEQ ID NO: 2. In an exemplary embodiment, an exemplary DNA aptamer may have a dissociation constant ($K_d$) between about 10 nM and about 190 nM. In an exemplary embodiment, an exemplary composition may further include a tag conjugated to the DNA aptamer. In an exemplary embodiment, the tag may include at least one of a therapeutic tag and a diagnostic tag.

In an exemplary embodiment, the diagnostic tag may include at least one of a radioactive substance, a dye, a contrast agent, a fluorophore molecule, a nanoparticle, a bioluminescent molecule, an affinity agent, and a magnetic agent. In an exemplary embodiment, the radioactive substance may include at least one of phosphorus-32 (32P), sulfur-35 (35S), and phosphorus-33 (33P). In an exemplary embodiment, the dye may include at least one of a cyanine dye and methylene blue. In an exemplary embodiment, the contrast agent may include at least one of gadolinium nanoparticles and superparamagnetic iron oxide nanoparticles.

In an exemplary embodiment, the fluorophore molecule may include at least one of acridine orange, auramine, crystal violet, malachite green, porphin, phthalocyanine, cresyl violet, fluorescein, rhodamine, green fluorescent dye, eosin, cyanine derivatives, blue fluorescent DNA dye, a green fluorescent protein (GFP), and 4',6-diamidino-2-phenylindole (DAPI). In an exemplary embodiment, the bioluminescent molecule may include luciferase. In an exemplary embodiment, the magnetic agent may include a magnetic bead. In an exemplary embodiment, the affinity tag may include at least one of a streptavidin/biotin-based tag, a polyhistidine tag, and a maltose-binding protein (MBP) tag.

In an exemplary embodiment, the nanoparticle may include at least one of superparamagnetic nanoparticles, gold nanoparticles, carbon nanotubes, silica nanoparticles, metal nanoparticles, graphene oxide nanoparticles, and metal-organic frameworks. In an exemplary embodiment, the therapeutic tag may include at least one of a chemotherapeutic drug, a toxin, an anti-cancer growth inhibitor compound, an anti-cancer siRNA, and an anti-cancer antagomir. In an exemplary embodiment, the chemotherapeutic drug may include at least one of cisplatin, paclitaxel, carboplatin, topotecan, 5-fluorouracil, mitomycin C, docetaxel, oxaliplatin, epirubicin, cyclophosphamide, methotrexate, doxorubicin, and irinotecan.

In an exemplary embodiment, the HPV16-positive tumor cells may include at least one of HPV16-positive cervical cancer cells, HPV16-positive head and neck cancer cells, HPV16-positive oropharynx cancer cells, HPV16-positive anal cancer cells, HPV16-positive vaginal cancer cells, HPV16-positive penile cancer cells, HPV16-positive vulvar cancer cells, HPV16-positive breast cancer cells, and HPV16-positive gastrointestinal cancer cells.

In another general aspect, the present disclosure describes an exemplary method for detecting HPV16-positive tumor cells in a biological sample. In an exemplary embodiment, an exemplary method may include putting the biological sample in contact with an exemplary composition and determining the presence of the HPV16-positive tumor cell in the biological sample responsive to detecting the DNA aptamer bound to the HPV16-positive tumor cell. In an exemplary embodiment, the composition may include an exemplary DNA aptamer and a diagnostic tag conjugated to the DNA aptamer. In an exemplary embodiment, an exemplary DNA aptamer may include one of SEQ ID NO: 1 and SEQ ID NO: 2.

In an exemplary embodiment, detecting the binding of the DNA aptamer to the HPV16-positive tumor cell may include detecting a signal generated by the diagnostic tag responsive to binding the DNA aptamer to the HPV16-positive tumor cells. In an exemplary embodiment, detecting the signal generated by the diagnostic tag may include detecting the signal generated by the diagnostic tag by conducting at least one of a chemiluminescent assay, a fluorescent assay, enzyme-linked apta-sorbent assay (ELASA), radioimmunoassay, a western blot assay, an apta-precipitation assay, an apta-histochemical assay, an immunochromatographic assay, a dot blot assay, a slot blot assay, confocal imaging, laser scanning microscopy, and flow cytometry. In an exemplary embodiment, putting the biological sample in contact with the composition may include putting at least one of a blood sample, a plasma sample, a serum sample, a fecal sample, a urine sample, a cervix sample, and a semen sample in contact with the composition.

In another general aspect, the present disclosure describes an exemplary method for targeting HPV16-positive tumor cells in a subject. In an exemplary embodiment, an exemplary method may include administering an exemplary composition to the subject. In an exemplary embodiment, the composition may include an exemplary DNA aptamer and a tag conjugated to an exemplary DNA aptamer. In an exemplary embodiment, an exemplary DNA aptamer may include one of SEQ ID NO: 1 and SEQ ID NO: 2. In an exemplary embodiment, the tag may include at least one of a diagnostic tag and a therapeutic tag. In an exemplary embodiment, an exemplary method for targeting HPV16-positive tumor cells in a subject may further include killing the HPV16-positive tumor cells in the subject by conducting at least one of magnetic hyperthermia, photodynamic therapy, and photothermal therapy.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
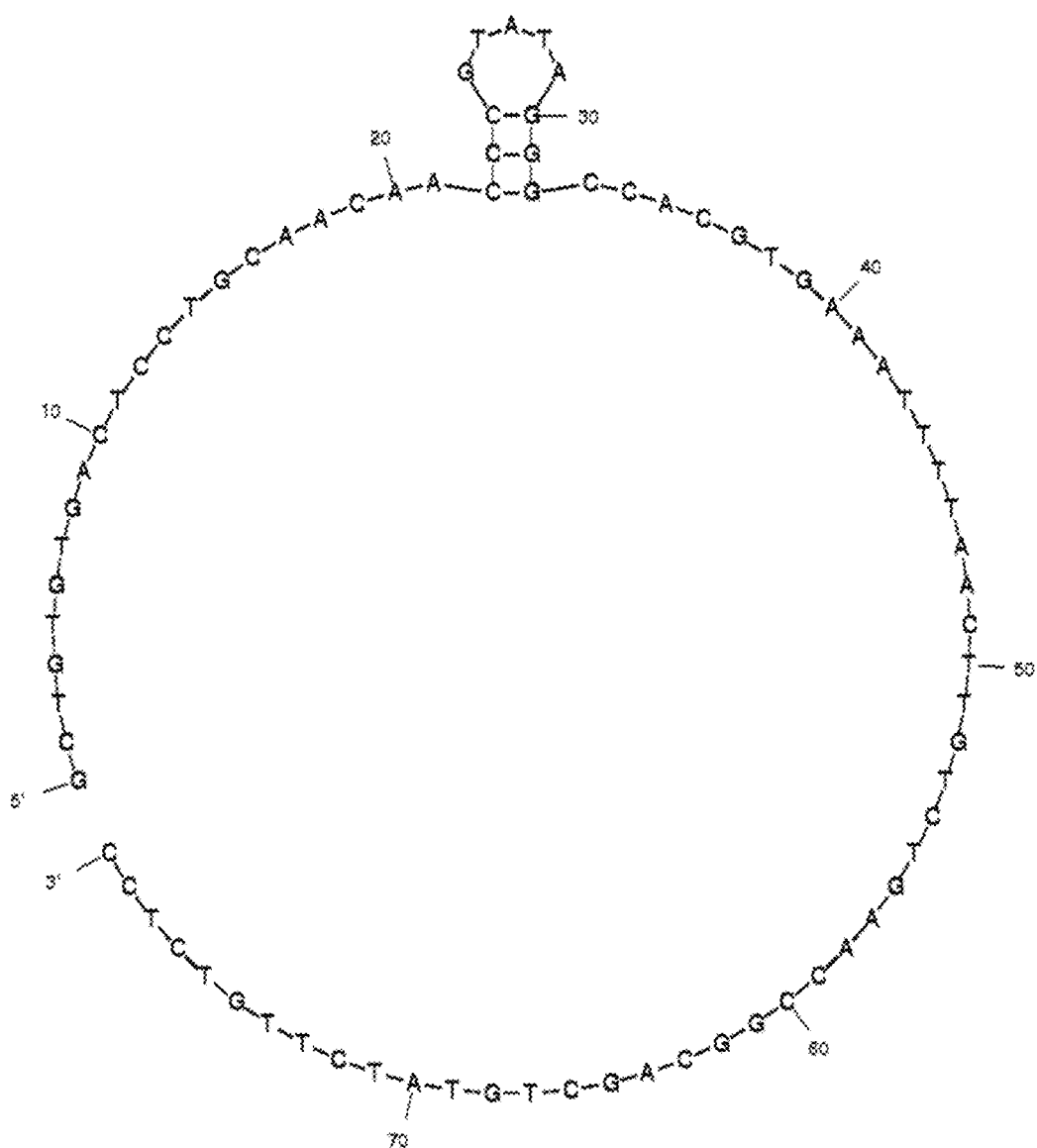
FIG. 1A illustrates a schematic view of a secondary structure of a DNA aptamer (SEQ ID NO: 1) against HPV16-positive tumor cells, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Utilizing exemplary aptamers for targeting tumor cells may aid in increasing sensitivity, specificity, and speed of the diagnostic and therapeutic procedures. The exemplary aptamers' ability to fold into unique and stable secondary structures may be exploited to recognize and bind specific target cells. Different features of an exemplary aptamer, such as small size, ease of synthesis, lack of immunogenicity, and ability to penetrate solid tumors, make aptamers a suitable candidate for targeted therapy, diagnosis, and theragnostic applications.

Disclosed herein is an exemplary composition for binding to human papillomavirus type 16 (HPV16)-positive tumor cells. An exemplary composition may include an exemplary DNA aptamer. In an exemplary embodiment, an exemplary DNA aptamer may include one of SEQ ID NO: 1 and SEQ ID NO: 2. In an exemplary embodiment, an exemplary DNA aptamer may specifically bind to a surface protein on the HPV16-positive tumor cells. In an exemplary embodiment, an exemplary DNA aptamer may not bind to HPV18-positive tumor cells. In an exemplary embodiment, an exemplary DNA aptamer may have a dissociation constant ($K_d$) between about 10 nM and about 190 nM. In an exemplary embodiment, an exemplary DNA aptamer of SEQ ID NO: 1 may have a dissociation constant ($K_d$) of about 52.07 nM. In an exemplary embodiment, an exemplary DNA aptamer of SEQ ID NO: 1 may have 80 nucleotides. In an exemplary embodiment, an exemplary DNA aptamer of SEQ ID NO: 2 may have a dissociation constant ($K_d$) of about 166.5 nM. In an exemplary embodiment, an exemplary DNA aptamer of SEQ ID NO: 2 may have 83 nucleotides.

FIG. 1A illustrates a schematic view of a secondary structure of a DNA aptamer (SEQ ID NO: 1) against HPV16-positive tumor cells, consistent with one or more exemplary embodiments of the present disclosure. Referring to FIG. 1A, exemplary DNA aptamer (SEQ ID NO: 1) may have a stem-loop structure with a minimum free energy of about −2.034 kcal/mol at a temperature of about 37° C. in the presence of sodium ions ($Na^+$) with a concentration of about 137 mM and magnesium ions ($Mg^+$) with a concentration of about 0.5 mM.

Figure 1B:
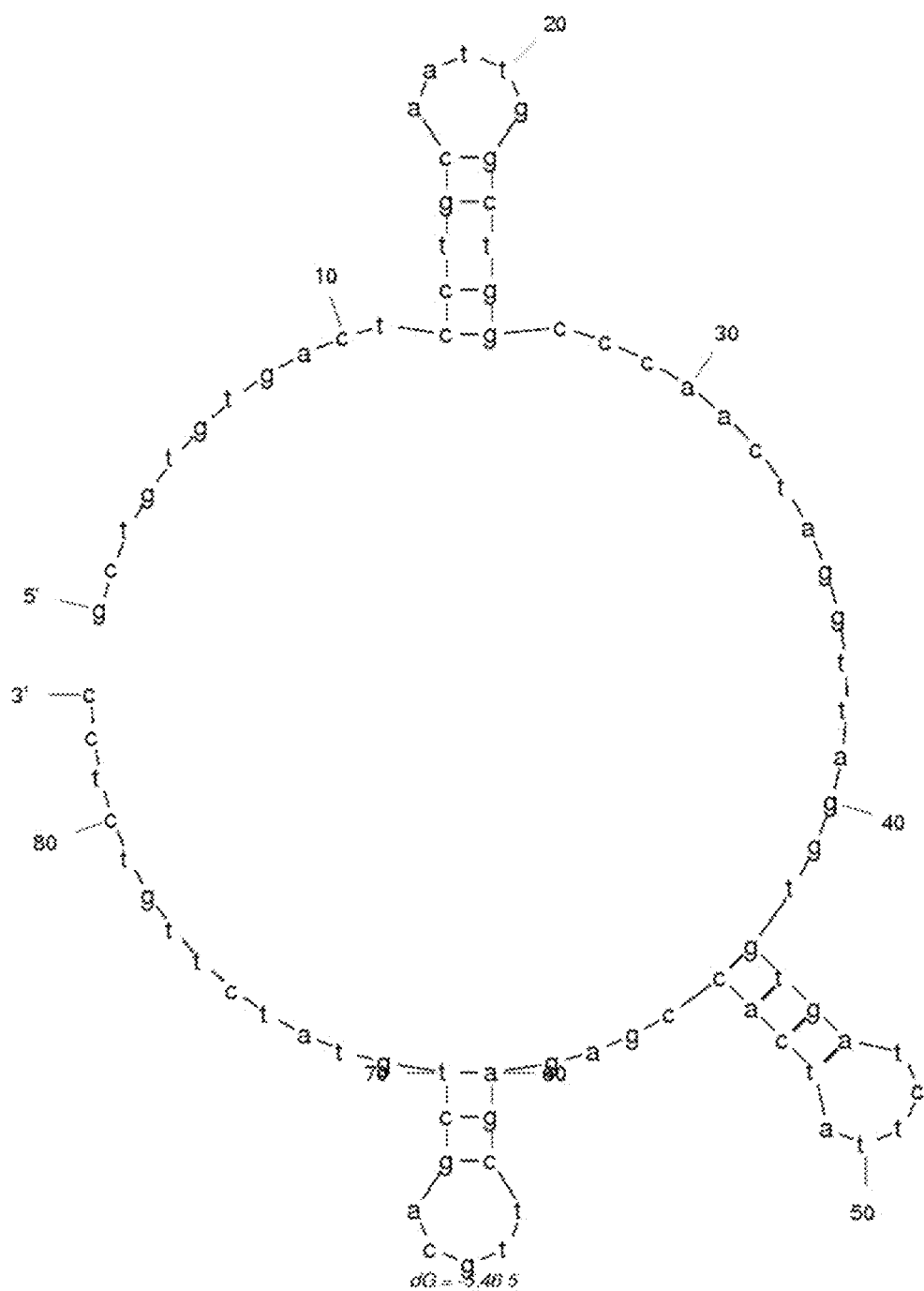
FIG. 1B illustrates a schematic view of a secondary structure of a DNA aptamer (SEQ ID NO: 2) against HPV16-positive tumor cells, consistent with one or more exemplary embodiments of the present disclosure.

FIG. 1B illustrates a schematic view of a secondary structure of a DNA aptamer (SEQ ID NO: 2) against HPV16-positive tumor cells, consistent with one or more exemplary embodiments of the present disclosure. Referring to FIG. 1B, exemplary DNA aptamer (SEQ ID NO: 2) may have a stem-loop structure with a minimum free energy of about −5.465 kcal/mol at a temperature of about 37° C. in the presence of $Na^+$ with a concentration of about 137 mM and $Mg^{2+}$ with a concentration of about 0.5 mM.

In an exemplary embodiment, an exemplary composition may further include a tag conjugated to the DNA aptamer. In an exemplary embodiment, the tag may include at least one of a therapeutic tag and a diagnostic tag. In an exemplary embodiment, the diagnostic tag may include at least one of a radioactive substance, a dye, a contrast agent, a fluorophore molecule, a nanoparticle, a bioluminescent molecule, an affinity agent, and a magnetic agent. In an exemplary embodiment, the radioactive substance may include at least one of phosphorus-32 (32P), sulfur-35 (35S), and phosphorus-33 (33P).

In an exemplary embodiment, the dye may include at least one of a cyanine dye and methylene blue. In an exemplary embodiment, the contrast agent may include at least one of gadolinium nanoparticles and superparamagnetic iron oxide nanoparticles. In an exemplary embodiment, the fluorophore molecule may include at least one of acridine orange, auramine, crystal violet, malachite green, porphin, phthalocyanine, cresyl violet, fluorescein, rhodamine, green fluorescent dye, eosin, cyanine derivatives, blue fluorescent DNA dye, a green fluorescent protein (GFP), and 4',6-diamidino-2-phenylindole (DAPI).

In an exemplary embodiment, the bioluminescent molecule may include luciferase. In an exemplary embodiment, the magnetic agent may include a magnetic bead. In an exemplary embodiment, the affinity tag may include at least one of a streptavidin/biotin-based tag, a polyhistidine tag, and a maltose-binding protein (MBP) tag. In an exemplary embodiment, the nanoparticle may include at least one of superparamagnetic nanoparticles, gold nanoparticles, carbon nanotubes, silica nanoparticles, metal nanoparticles, graphene oxide nanoparticles, and metal-organic frameworks.

In an exemplary embodiment, an exemplary composition may be used for targeted drug delivery to HPV16-positive tumor cells. In an exemplary embodiment, the therapeutic tag may include at least one of a chemotherapeutic drug, a toxin, an anti-cancer growth inhibitor compound, an anti-cancer siRNA, and an anti-cancer antagomir. In an exemplary embodiment, the chemotherapeutic drug may include at least one of cisplatin, paclitaxel, carboplatin, topotecan, 5-fluorouracil, mitomycin C, docetaxel, oxaliplatin, epirubicin, cyclophosphamide, methotrexate, doxorubicin, and irinotecan. In an exemplary embodiment, an exemplary composition may further include a pharmaceutical carrier. In an exemplary embodiment, the carrier may include at least one of poly (lactic-co-glycolic acid) (PLGA) nanoparticles, hydrogels, micelles, and liposomal nanoparticles.

In an exemplary embodiment, the HPV16-positive tumor cells may include at least one of HPV16-positive cervical cancer cells, HPV16-positive head and neck cancer cells, HPV16-positive oropharynx cancer cells, HPV16-positive anal cancer cells, HPV16-positive vaginal cancer cells, HPV16-positive penile cancer cells, HPV16-positive vulvar cancer cells, HPV16-positive breast cancer cells, and HPV16-positive gastrointestinal cancer cells.

Figure 2:
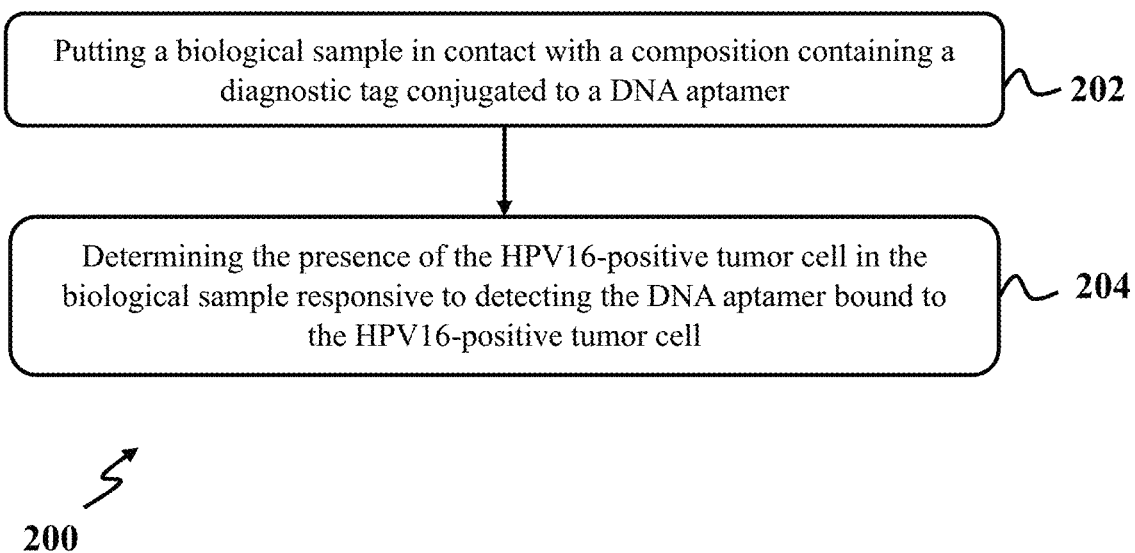
FIG. 2 illustrates a flowchart of an exemplary method for detecting human papillomavirus type 16 (HPV16)-positive tumor cells in a biological sample, consistent with one or more exemplary embodiments of the present disclosure.

An exemplary composition containing exemplary DNA aptamer (similar to exemplary DNA aptamers presented in FIGS. 1A and 1B) may be used for the in-vitro diagnosis of the HPV16-positive tumor cells. FIG. 2 illustrates a flowchart of an exemplary method 200 for detecting human papillomavirus type 16 (HPV16)-positive tumor cells in a biological sample using an exemplary composition containing exemplary DNA aptamer, consistent with one or more exemplary embodiments of the present disclosure. An exemplary method 200 may include putting the biological sample in contact with an exemplary composition containing a diagnostic tag conjugated to exemplary DNA aptamer (step 202) and determining the presence of the HPV16-positive tumor cell in the biological sample responsive to detecting the DNA aptamer bound to the HPV16-positive tumor cell (step 204).

In further detail with respect to step 202, in an exemplary embodiment, putting the biological sample in contact with an exemplary composition may include forming aptamer-cell complexes between the DNA aptamer of the composition and an HPV16-positive tumor cell. In an exemplary embodiment, forming the aptamer-cell complexes between the DNA aptamer of the composition and the HPV16-positive tumor cell may include forming the aptamer-cell complexes between the DNA aptamer of the composition and the HPV16-positive tumor cell if the HPV16-positive tumor cell is present in the biological sample. In an exemplary embodiment, putting the biological sample in contact with the composition may include putting at least one of a blood sample, a plasma sample, a serum sample, a fecal sample, a urine sample, a cervix sample, and a semen sample in contact with the composition.

In further detail with respect to step 204, in an exemplary embodiment, detecting the DNA aptamer bound to the HPV16-positive tumor cell may include detecting a signal generated by the diagnostic tag responsive to binding the DNA aptamer to the HPV16-positive tumor cells. In an exemplary embodiment, the signal may include at least one of a fluorescent signal, a chemical signal, a biological signal, an electrochemical signal, and a physical signal. In an exemplary embodiment, detecting the signal generated by the diagnostic tag may include conducting at least one of a chemiluminescent assay, a fluorescent assay, enzyme-linked apta-sorbent assay (ELASA), radioimmunoassay, a western blot assay, an apta-precipitation assay, an apta-histochemical assay, an immunochromatographic assay, a dot blot assay, a slot blot assay, confocal imaging, laser scanning microscopy, and flow cytometry. In an exemplary embodiment, exemplary DNA aptamers may be immobilized on a support such as beads for detecting HPV16-positive tumor cells in the biological sample.

An exemplary composition may also be used for in-vivo targeting HPV16-positive tumor cells in diagnostic, therapeutic, and theragnostic applications. In an exemplary embodiment, the present disclosure describes an exemplary method for targeting HPV16-positive tumor cells in a subject by administering an exemplary composition to the subject. In an exemplary embodiment, an exemplary composition may include an exemplary DNA aptamer and a tag conjugated to the DNA aptamer. In an exemplary embodiment, the tag may include at least one of a diagnostic tag and a therapeutic tag. In an exemplary embodiment, the therapeutic tag may help in killing or treating the HPV16-positive tumor cells. In an exemplary embodiment, the diagnostic tag may help in diagnosing the HPV16-positive tumor cells by generating a signal responsive to binding exemplary DNA aptamer to HPV16-positive tumor cells. In an exemplary embodiment, administering an exemplary composition to the subject may include administering an exemplary composition to the subject through different administration routes, including at least one of subcutaneous administration, intramuscular administration, and intravenous administration.

In an exemplary embodiment, an exemplary method for targeting HPV16-positive tumor cells in a subject may further include killing the HPV16-positive tumor cells in the subject by conducting at least one of magnetic hyperthermia, photodynamic therapy, and photothermal therapy. In an exemplary embodiment, an exemplary method for targeting HPV16-positive tumor cells in a subject may further include tracking the HPV16-positive tumor cells in the subject using an aptasensor and magnetic resonance imaging (MRI). In an exemplary embodiment, the aptasensor may track the HPV16-positive cells in the subject by sensing the HPV16-positive tumor cells utilizing exemplary DNA aptamer and generating a signal using a diagnostic tag.

EXAMPLES

Example 1: Identification of DNA Aptamers Against HPV16-Positive Tumor Cells Using the Cell-Selex Method In this example, exemplary DNA aptamers against HPV16-positive tumor cells were identified using the cell-SELEX method. The cell-SELEX method was performed through the steps of forming aptamer-cell complexes by adding a library of DNA aptamers to a human cervical carcinoma cell (CaSki cells) as the HPV16-positive tumor cells (binding step), isolating aptamer-cell complexes from unbound aptamers (partitioning step), separating bound aptamers from the cells (elution step), amplifying the bound aptamers through polymerase chain reaction (amplification step), and preparing the amplified aptamers for the next round of cell-SELEX (conditioning step).

The library of aptamers included a rich set of random single-stranded DNA sequences from which the DNA aptamers against HPV16-positive tumor cells were separated during the cell-SELEX process. Each aptamer in the library of aptamers had a nucleotide sequence of SEQ ID No. 3 with a central random region flanked by two overhangs with constant sequences at 5' and 3' ends. The central random region included between about 43 and about 46 nucleotides. The overhang at the 5' end was a binding region for a forward primer with a nucleotide sequence of SEQ ID No. 4. The overhang at the 3' end was a binding region for a phosphorylated reverse primer with a nucleotide sequence of SEQ ID No. 5.

The library of aptamers, forward primer, and the reverse primer were prepared with high-performance liquid chromatography (HPLC) purification with the optical absorbance concentration of about 3 (OD=3.0). To obtain labeled DNA aptamers for monitoring the progression of SELEX rounds, affinity determination, and characterization of the DNA aptamers, the aptamers of the library were amplified using the forward primer labeled with ATTO 647N fluorescent labels and the phosphorylated reverse primer in the polymerase chain reaction (PCR) and.

To provide a negative control for the cell-SELEX method, the CaSki (CRL1550) cells were cultured in a cell culture plate, followed by 24 hours incubation in a $CO_2$ incubator at a temperature of about 37° C. The CaSki cells were then washed twice with a washing buffer containing Dulbecco's phosphate-buffered saline (DPBS), $MgCl_2$ with a concentration of about 5 mM, and glucose with a concentration of about 4.5 g/L. After washing the CaSki cells, the cell culture plate may be filled with a binding buffer containing DPBS, $MgCl_2$ with a concentration of about 5 mM, glucose with a concentration of about 4.5 g/L, and bovine serum albumin (BSA) with a concentration of about 1 g/L. Then, the CaSki cells were detached utilizing a scraper and heated up to a temperature of about 95° C. for a time period of about 10 minutes and centrifuged at a speed of about 13100 G for a time period of about 5 minutes. After centrifuging, the supernatant was collected into a microtube and used as a negative control in the cell-SELEX.

The selection of DNA aptamer was done by performing several rounds of cell-SELEX. In the binding step of the first round of cell-SELEX, a solution of a library of DNA aptamers was added to the CaSki cell line to form aptamer-cell complexes. The solution of the library of DNA aptamers was prepared by dissolving the library of DNA aptamers with an amount of about 5 nmol in the binding buffer with a volume of about 5 ml at a temperature of about 95° C. for a time period of about 5 minutes. Then, the aptamer solution was cooled on ice.

The CaSki cells as the target cells were cultured in a cell culture plate with a size of about 2 cm x 10 cm for a time period of about 48 hours. After obtaining 95% confluency, the CaSki cells were washed three times using the washing buffer with a volume of about 3 ml. The aptamer solution was then slowly added to the CaSki cells and incubated at a temperature of about 4° C. for a time period of about 1 hour in a shaker incubator. During incubation, some aptamers of the library were able to bound to the CaSki cells and formed aptamer-cell complexes.

In the partitioning step, aptamer-cell complexes were isolated from unbound aptamers by washing the cells three times and using the washing buffer with a volume of about 3 ml. The number of washes and the amount of washing buffer were gradually increased until round 16 of cell-SELEX. During the partitioning step, high-affinity aptamers were selected by removing low-affinity aptamers from the bound aptamers. In the elution step, the bound aptamers were separated from the target cells. For separating the oligonucleotides from the target cells, the CaSki cells were scraped using a cell scraper and resuspended in a microtube containing distilled water with a volume between about 500 μl and about 700 μl. The microtube was heated up to a temperature of about 95° C. for a time period of about 10 minutes, and the supernatant containing high-affinity aptamers was collected after centrifugation at a speed of about 13100 G.

In the amplification step, the high-affinity aptamers were amplified by performing at least two times of PCR per round of cell-SELEX. First, the number of PCR cycles was optimized between 4 and 18, then preparative PCR at the obtained cycle was done to enrich the oligonucleotides pool for the next round of cell-SELEX. In the conditioning step, the PCR products were then purified using a PCR purification kit. The double-stranded (ds) PCR products were converted to single-stranded (ss) DNA as DNA aptamers using λ-exonuclease digestion of the phosphorylated dsDNA. The DNA aptamers were then purified using a purification kit.

The selection process was continued for about 16 rounds of cell-SELEX until significant enrichment was obtained for the CaSki cells as the target cells, but not for the A2780 cells of the negative control. From $2^{nd}$ round to $16^{th}$ round, the DNA aptamer pool of the previous round was used with a concentration of between 30 nM and 40 nM. The target cell's incubation time with the DNA aptamer pool was gradually decreased from one hour to 30 minutes. From the second round until the end of the cell-SELEX, the binding buffer was supplemented with yeast tRNA at a concentration between about 0.8 mg/ml and about 1.2 mg/ml to increase the specificity of DNA aptamers. From the sixth round until the end of the cell-SELEX, heat-inactivated fetal bovine serum (FBS) with a volume concentration of about 5% was added to the binding buffer and gradually increased toward the $16^{th}$ round up to about 20%.

For obtaining aptamers with high specificity, at the same time, not losing oligonucleotides at preliminary rounds, the A2780 cell line was used in the third round for the counter selection; as a result, cross-reactive DNA aptamers which bound to A2780 cells as the negative control cells were removed. During counter selection, the A2780 cells were treated with the DNA aptamer pool, and then the unbound DNA aptamers in the supernatant of the A2780 cells were poured onto the CaSki cells. The incubation time with A2780 cells increased from 30 minutes in the third round to about 1.5 hours in the 16$^{th}$ round. The number of target cells decreased, and the number of control cells increased from the 15$^{th}$ round.

The progress of the DNA aptamer selection was monitored by incubating ATTO-labeled DNA aptamers of each round of cell-SELEX with the CaSki cells and the A2780 cells and then measuring the fluorescence intensity of each group. The labeled DNA aptamers were obtained through PCR using ATTO-labelled forward primer. Flow cytometry samples were prepared using a DNA aptamer pool with a concentration between about 130 nM and about 180 nM for each round of cell-SELEX. After each round of cell-SELEX, a mixture was formed by adding the ATTO-labelled DNA aptamer pool of each round to the binding buffer and heated up to a temperature of about 95° C. for a time period of about 5 minutes. The mixture was immediately cooled on ice and supplemented with 15% FBS and tRNA.

The CaSki cells and the A2780 cells were cultured in 12-well plates for 48 hours and then treated with DNA aptamer pools of different rounds of cell-SELEX for a time period of about 35 minutes at a temperature of about 4° C. on a rocker in the dark. After incubation, the cells were washed with the washing buffer twice and scraped using a cell scraper. The cells were then resuspended in DPBS with a volume of about 200 and the fluorescence intensity of the cells was measured using a flow cytometer.

Figure 3A:
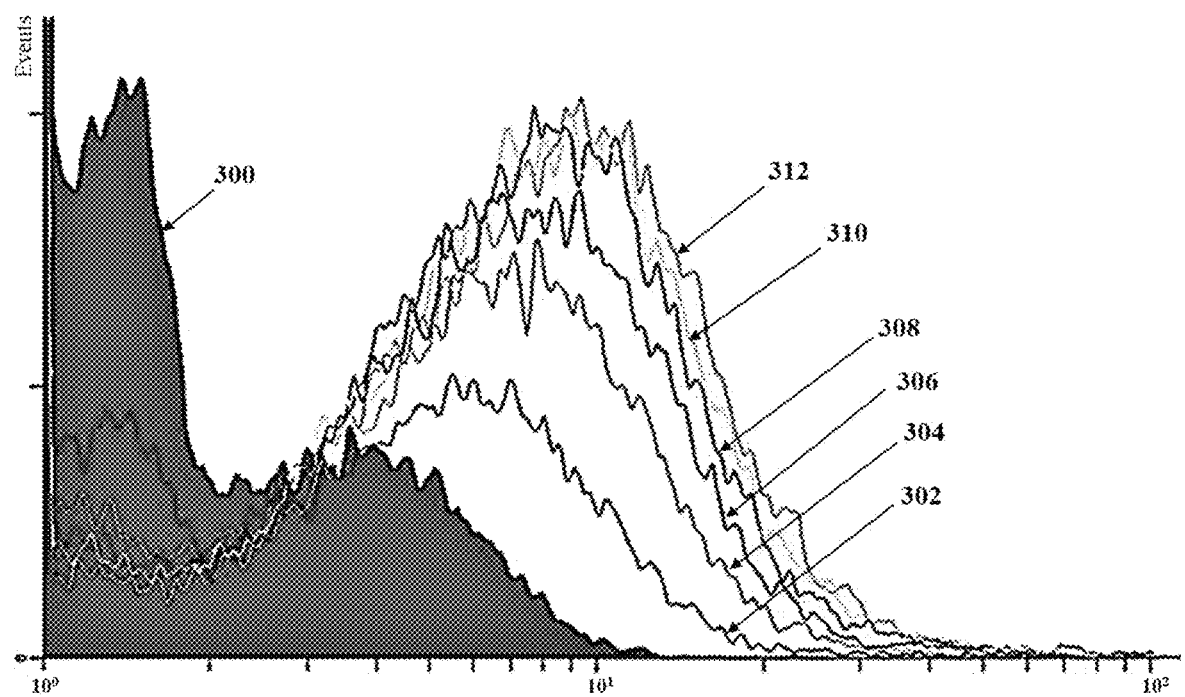
FIG. 3A illustrates flow cytometry graphs of binding assay of different groups against HPV16-positive tumor cells, including target cells without any DNA aptamer, a library of DNA aptamer, and DNA aptamers of three, six, nine, twelve, and thirteen rounds of cell-SELEX, consistent with one or more exemplary embodiments of the present disclosure.
Figure 3B:
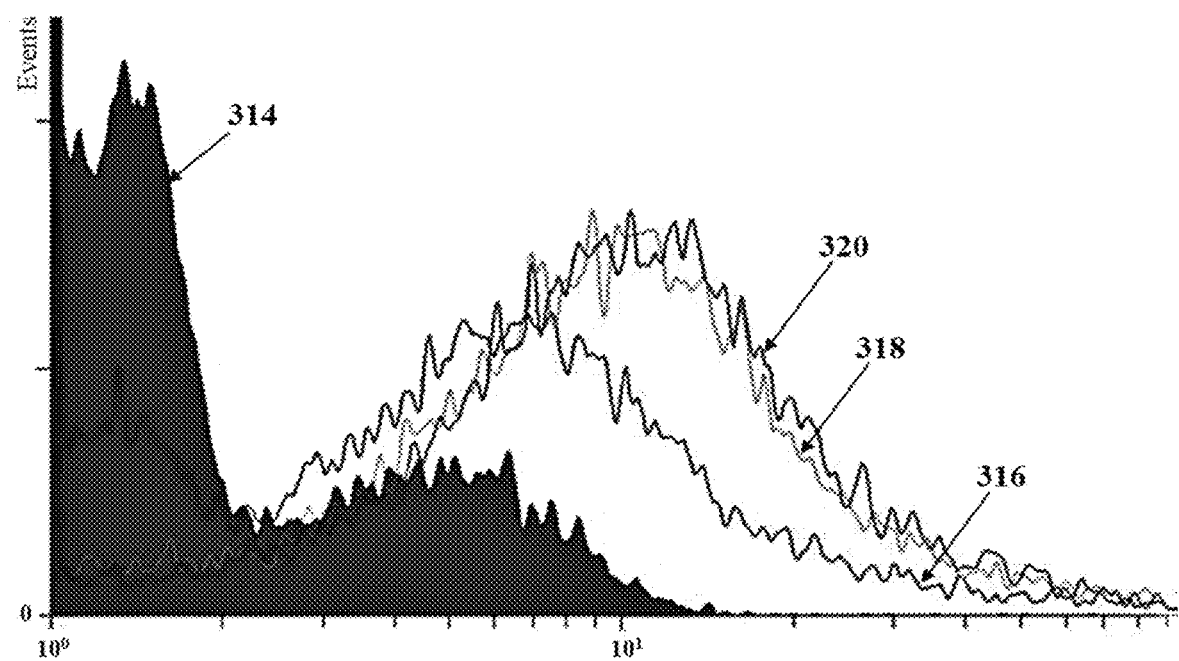
FIG. 3B illustrates flow cytometry graphs of binding assay of different groups against HPV16-positive tumor cells, including target cells, a library of DNA aptamers, and DNA aptamers of fifteen and sixteen cell-SELEX rounds, consistent with one or more exemplary embodiments of the present disclosure.

FIG. 3A illustrates flow cytometry graphs of binding assay of different groups against HPV16-positive tumor cells, including target cells without any DNA aptamer 300, a library of DNA aptamer 302, and DNA aptamers of three rounds 304, six rounds 306, nine rounds 308, twelve rounds 310, and thirteen rounds 312 of cell-SELEX, consistent with one or more exemplary embodiments of the present disclosure. FIG. 3B illustrates flow cytometry graphs of binding assay of different groups against HPV16-positive tumor cells, including target cells 314, the library of DNA aptamers 316, and DNA aptamers of fifteen rounds 318, and sixteen rounds 320 of cell-SELEX, consistent with one or more exemplary embodiments of the present disclosure. Referring to FIGS. 3A-3B, the fluorescence intensity of the DNA aptamer pools increased by increasing the cell-SELEX method rounds, which indicates enrichment of the DNA aptamers with high-affinity for CaSki cells. Also, the flow cytometry graphs of DNA aptamers of fifteen rounds 318 and sixteen rounds 320 of cell-SELEX significantly overlapped, which indicates that the cell-SELEX method with 16 rounds was enough for identifying the specific DNA aptamers with high affinity.

After performing the 16$^{th}$ round of the cell-SELEX, the obtained DNA aptamer pool was amplified with unlabeled primers and cloned into a pTZ57R/T plasmid using the TA cloning kit. After cloning, *Escherichia coli* (*E. coli*) bacteria were transformed with cloned plasmids. White and pale blue colonies were picked for colony PCR to confirm the oligonucleotide sequence of DNA aptamers. The bacterial plasmids were then purified using a plasmid extraction kit, and about 66 purified plasmids were sent for DNA sequencing. Sequence alignment was then performed with the sequence alignment program ClustalX. Nucleotide sequences were also aligned and compared using DNAMAN software. The selected DNA aptamers were grouped into five families based on their sequence homology, and some DNA aptamers from each family were selected for further characterization.

Example 2: Binding Affinity of Selected DNA Aptamers to HPV16-Positive Tumor Cells In this example, the binding affinity of exemplary DNA aptamers, which were selected during the cell-SELEX method described in EXAMPLE 1, were determined using flow cytometry. The DNA aptamers were selected from each family to determine the cell binding affinity against the CaSki cells as the HPV16-positive target cell and human ovarian carcinoma (A2780) cell line as the negative control. At first, the selected DNA aptamers were labeled by amplifying with an ATTO 647N-labeled forward primer using the nested-PCR method. Labeled double-stranded (ds) PCR products produced during the nested-PCR were converted to labeled single-stranded (ss) as labeled DNA aptamers.

The CaSki cells as the target cells and the A2780 cells as the control cells were cultured in 12-well plated for about 48 hours to reach a 95% confluency. The cells' supernatants were removed, and the cells were washed twice with 400 μl washing buffer. The cells were then blocked for avoiding non-specific binding with a blocking mixture containing 15% fetal bovine serum (FBS), 4 μl tRNA, and 2 μl salmon sperm DNA in 400 μl binding buffer for each well. The blocking mixture was then heated at a temperature of about 95° C. for a time period of about 5 minutes and immediately cooled at a temperature of about 4° C. for a time period of about 10 minutes. The blocking mixture with a volume of about 400 μl was adding to the cells. The cells were incubated in a shaker incubator with gentle shaking at a temperature of about 37° C. for a time period of about 45 minutes. Then, the cells were washed twice with 400 μl washing buffer.

After blocking the cells, aptamer solutions were prepared by dissolving about 400 ng of each selected aptamer in the blocking mixture and heated at a temperature of about 95° C. for a time period of about 5 minutes and immediately cooled at a temperature of about 4° C. for a time period of about 10 minutes. Then, the cells were treated with the aptamer solutions and incubated at a temperature of about 37° C. for a time period of about 45 minutes in a shaker incubator. Then, the cells were washed twice with 400 μl washing buffer.

Figure 4A:
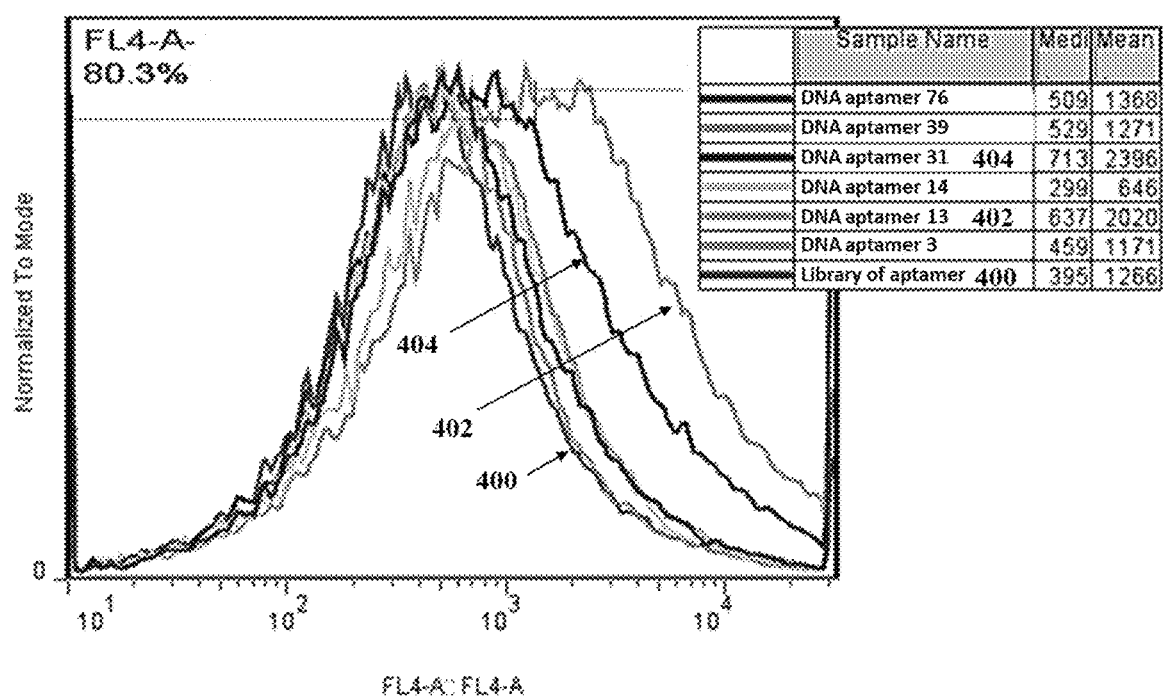
FIG. 4A illustrates flow cytometry graphs of binding assay of different groups, including DNA aptamer 76, DNA aptamer 39, DNA aptamer 14, DNA aptamer 31 (SEQ ID NO: 2), DNA aptamer 13 (SEQ ID NO: 1), DNA aptamer 3, and library to human cervical carcinoma cells (CaSki cells) as HPV16-positive tumor cells, consistent with one or more exemplary embodiments of the present disclosure.

After washing the cells, the cells were scraped and resuspended in 300 μl DPBS, and the fluorescence intensity of each group was assessed using flow cytometry. FIG. 4A illustrates flow cytometry graphs of binding assay of different groups, including DNA aptamer 76, DNA aptamer 39, DNA aptamer 14, DNA aptamer 31 (SEQ ID NO: 2) 404, DNA aptamer 13 (SEQ ID NO: 1) 402, DNA aptamer 3, and library 400 to CaSki cells as the HPV16-positive tumor cells, consistent with one or more exemplary embodiments of the present disclosure. Referring to FIG. 4A, the flow cytometry graphs of the selected DNA aptamers, the AG13 DNA aptamer (SEQ ID NO: 1) 402, and the AG31 DNA aptamer (SEQ ID NO: 2) 404 significantly shifted to higher fluorescence intensity compared to the library of DNA aptamers 400 and had the highest affinity to the target cells.

Figure 4B:
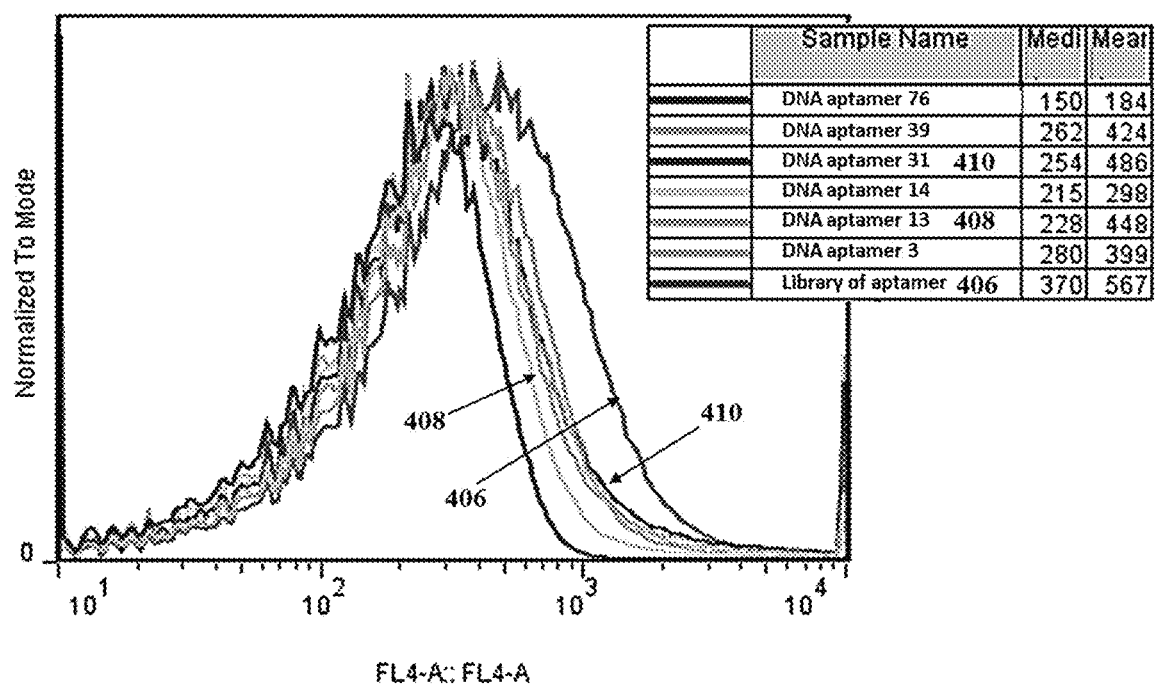
FIG. 4B illustrates flow cytometry graphs of binding assay of different groups, including DNA aptamer 76, DNA aptamer 39, DNA aptamer 14, DNA aptamer 31 (SEQ ID NO: 2), DNA aptamer 13 (SEQ ID NO: 1), DNA aptamer 3, and library to A2780 cells as a negative control, consistent with one or more exemplary embodiments of the present disclosure.

FIG. 4B illustrates flow cytometry graphs of binding assay of different groups, including DNA aptamer 76, DNA aptamer 39, DNA aptamer 14, DNA aptamer 31 (SEQ ID NO: 2) 410, DNA aptamer 13 (SEQ ID NO: 1) 408, DNA aptamer 3, and library 406 to A2780 cells as a negative control, consistent with one or more exemplary embodiments of the present disclosure. Referring to FIG. 4B, the flow cytometry graphs of the AG13 DNA aptamer (SEQ ID NO: 1) 408 and the AG31 DNA aptamer (SEQ ID NO: 2) 410 did not shift to higher fluorescence intensity compared to the library of DNA aptamers 406 and had the least affinity to the negative control cells.

As a result, the selected aptamers were AG13 DNA aptamer (SEQ ID NO: 1) and the AG31 DNA aptamer (SEQ ID NO: 2), which showed the highest affinity to the CaSki cells as the target cells and the least affinity to the A2780 cells as the control cells among the candidate DNA aptamers. The specific affinity of the AG13 DNA aptamer (SEQ ID NO: 1) and the AG31 DNA aptamer (SEQ ID NO: 2) was determined by repeating binding affinity assay using different concentrations of DNA aptamer up to 300 nM. Therefore, the CaSki cells were incubated with different concentrations of selected DNA aptamers at a temperature of about 37° C. for 45 minutes in a shaker incubator with a speed of about 70 rounds per minute (RPM).

The cells were washed three times, with 400 µl washing buffer, scraped, and resuspended in 300 µl DPBS. The fluorescence intensity of each group was assessed using flow cytometry. In each DNA aptamer's concentration, the DNA aptamer's specific binding was calculated by subtracting the mean fluorescence intensity (MFI) of cells labeled with the selected aptamers from the MFI of the cells treated with the library of DNA aptamers, which is regarding as a control for non-specific bindings. As a result, each selected DNA aptamer's $K_d$ value was calculated using the selected DNA aptamer's dissociation curve.

Figure 5A:
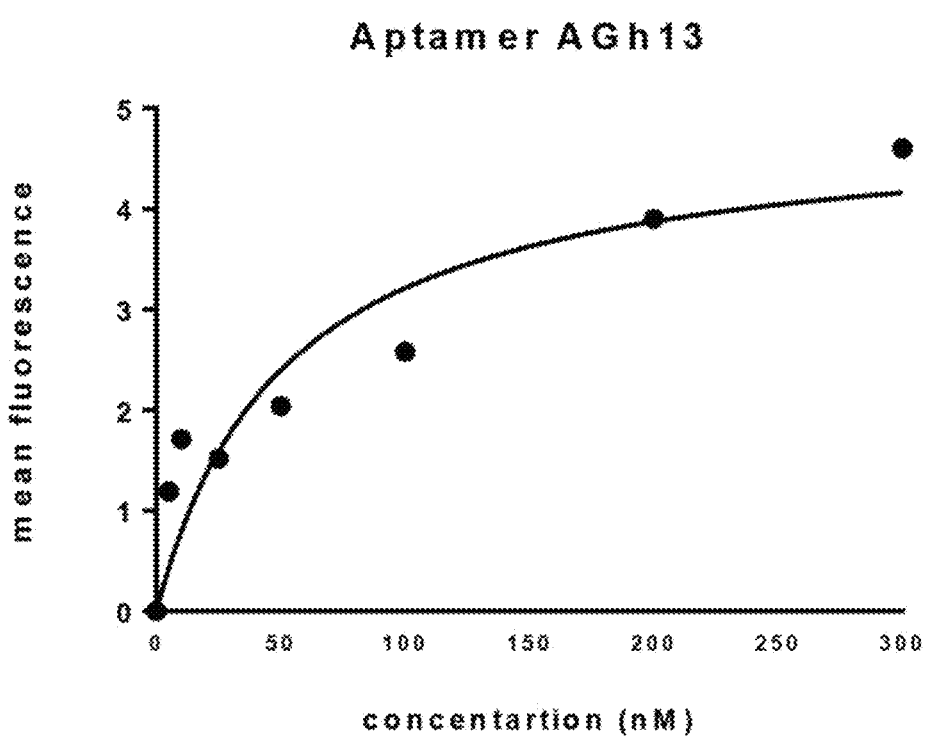
FIG. 5A illustrates a dissociation curve of the AG13 DNA aptamer (SEQ ID NO: 1), consistent with one or more exemplary embodiments of the present disclosure.
Figure 5B:
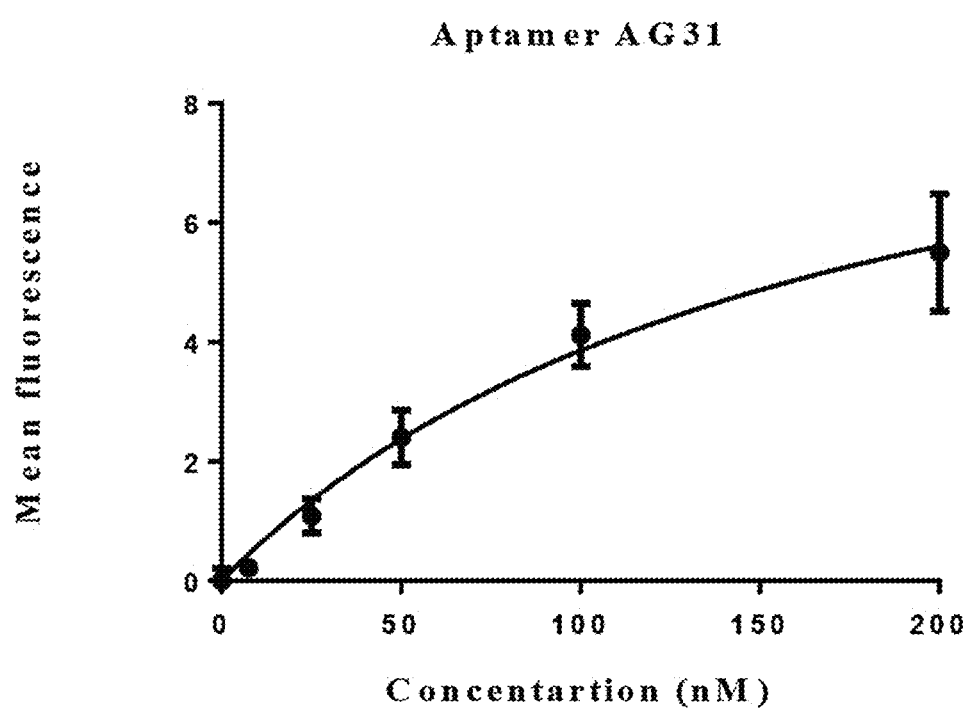
FIG. 5B illustrates a dissociation curve of the AG31 DNA aptamer (SEQ ID NO: 2), consistent with one or more exemplary embodiments of the present disclosure.

FIG. 5A illustrates a dissociation curve of the AG13 DNA aptamer (SEQ ID NO: 1) from CaSki cells, consistent with one or more exemplary embodiments of the present disclosure. Referring to FIG. 5A, the $K_d$ of the AG13 DNA aptamer (SEQ ID NO: 1), was calculated about 52.07 nM with $R^2$ of about 0.86 for CaSki cells as the HPV16-positive tumor cells. FIG. 5B illustrates a dissociation curve of the AG31 DNA aptamer (SEQ ID NO: 2) from CaSki cells, consistent with one or more exemplary embodiments of the present disclosure. Referring to FIG. 5B, the $K_d$ of the AG31 DNA aptamer (SEQ ID NO: 2), was 166.5 nM with $R^2$ of about 0.9921 for CaSki cells as the HPV16-positive tumor cells.

Example 3: Specificity of Selected DNA Aptamers Against HPV16-Positive Tumor Cells In this example, specificity of the selected aptamers to different cell lines including HPV18-positive human cervical cancer cell line (HeLa), normal human umbilical vein endothelial cell line (HUVEC), human gastric carcinoma cell line (EPG85-257P), human hepatocellular carcinoma cell line (HepG2), human lung cancer cell line (A549), human breast adenocarcinoma cell line (MCF-7), and human normal fibroblast-like cervical cell line (HNCF-PI 52) were determined. To conduct the specificity test, each of the selected DNA aptamers and the library of DNA aptamers with a concentration of about 100 nM was added to each cell line, cultured in a 24-well plate for a time period of about 48 hours. Selected aptamers were incubated with different cell lines in 12-well plates for about 45 minutes at a temperature of about 37° C. on a shaker. After washing the cells with the washing buffer, the cells were scraped and added to 300 µl DPBS, and the fluorescence intensity of the cells was assessed using flow cytometry.

Figure 6A:
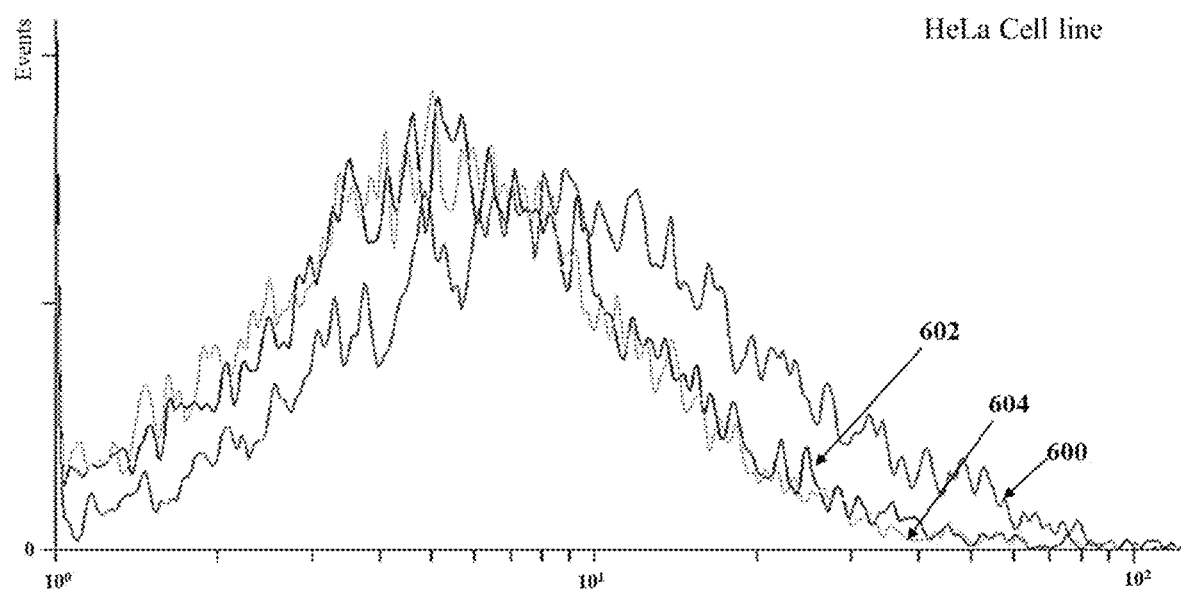
FIG. 6A illustrates flow cytometry graphs of the specificity assay of the AG13 DNA aptamer (SEQ ID NO:1), the AG31 DNA aptamer (SEQ ID NO: 2), and the library of DNA aptamers against human cervical cancer cell line (HeLa), consistent with one or more exemplary embodiments of the present disclosure.
Figure 6B:
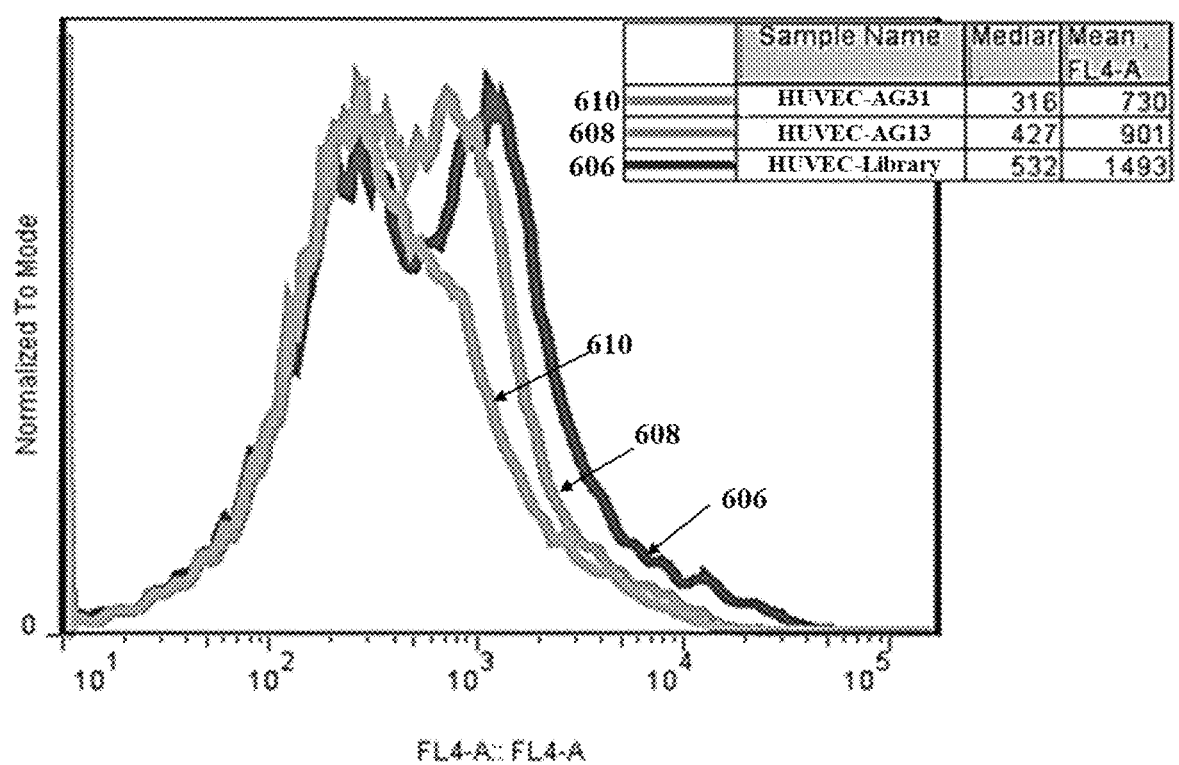
FIG. 6B illustrates flow cytometry graphs of the specificity assay of the AG13 DNA aptamer (SEQ ID NO:1), the AG31 DNA aptamer (SEQ ID NO: 2), and the library of DNA aptamers against normal human umbilical vein endothelial cell line (HUVEC), consistent with one or more exemplary embodiments of the present disclosure.

FIG. 6A illustrates flow cytometry graphs of the specificity assay of the AG13 DNA aptamer (SEQ ID NO:1) 602, the AG31 DNA aptamer (SEQ ID NO: 2) 604, and the library of DNA aptamers 600 against the HeLa cell line, consistent with one or more exemplary embodiments of the present disclosure. FIG. 6B illustrates flow cytometry graphs of the specificity assay of the AG13 DNA aptamer (SEQ ID NO:1) 608, the AG31 DNA aptamer (SEQ ID NO: 2) 610, and the library of DNA aptamers 606 against normal human umbilical vein endothelial cell line (HUVEC), consistent with one or more exemplary embodiments of the present disclosure.

Figure 6C:
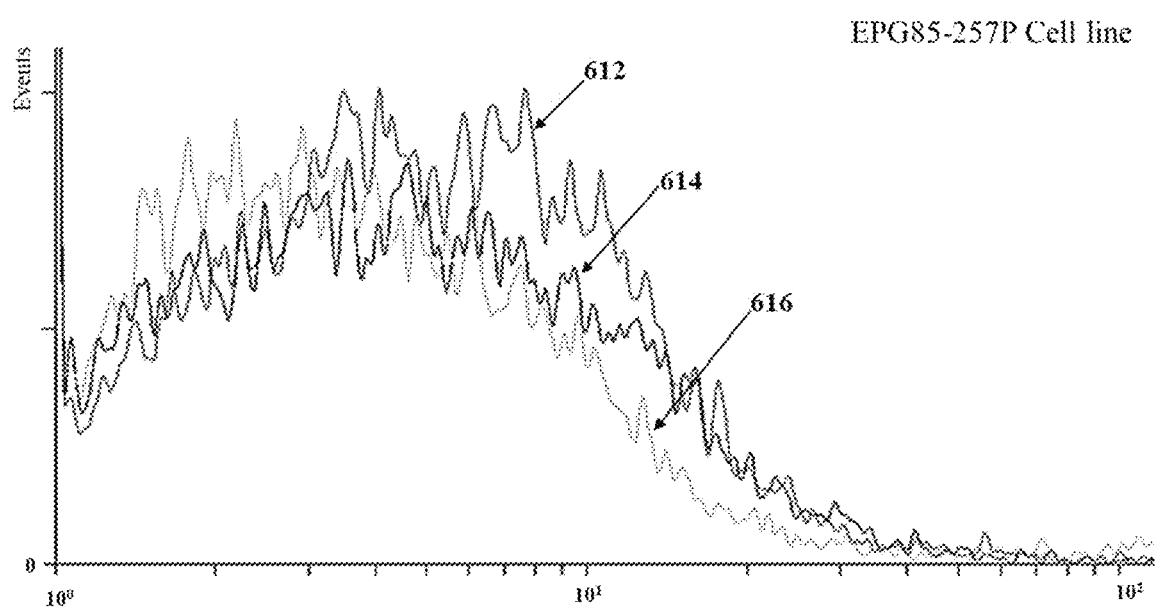
FIG. 6C illustrates flow cytometry graphs of the specificity assay of the AG13 DNA aptamer (SEQ ID NO:1), the AG31 DNA aptamer (SEQ ID NO: 2), and the library of DNA aptamers against human gastric adenocarcinoma cell line (EPG85-257P), consistent with one or more exemplary embodiments of the present disclosure.
Figure 6D:
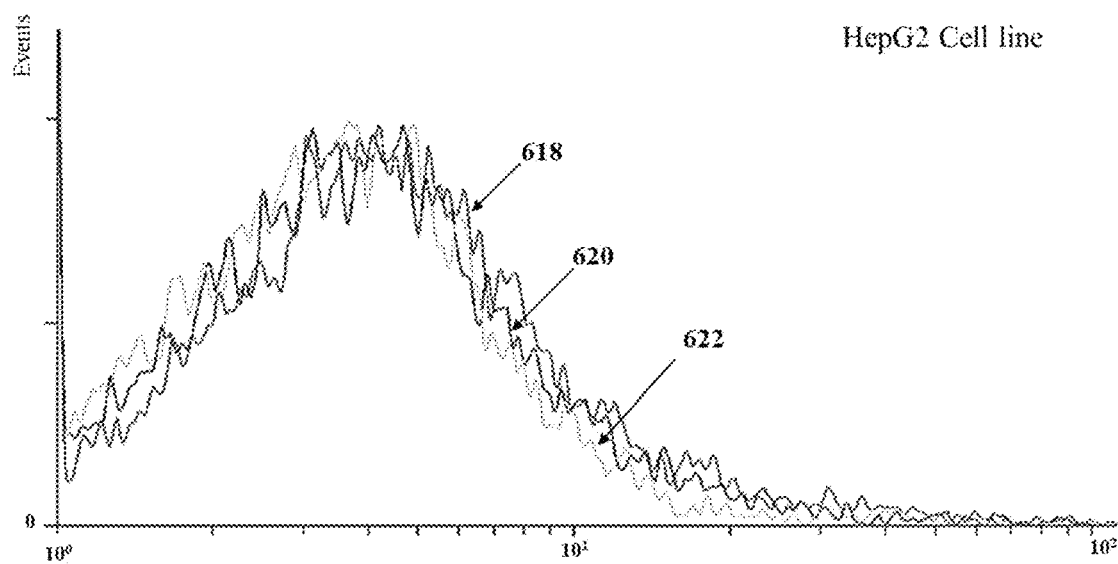
FIG. 6D illustrates flow cytometry graphs of the specificity assay of the AG13 DNA aptamer (SEQ ID NO:1), the AG31 DNA aptamer (SEQ ID NO: 2), and the library of DNA aptamers against human hepatocellular carcinoma cell line (HepG2), consistent with one or more exemplary embodiments of the present disclosure.

FIG. 6C illustrates flow cytometry graphs of the specificity assay of the AG13 DNA aptamer (SEQ ID NO:1) 614, the AG31 DNA aptamer (SEQ ID NO: 2) 616, and the library of DNA aptamers 612 against human gastric adenocarcinoma cell line (EPG85-257P), consistent with one or more exemplary embodiments of the present disclosure. FIG. 6D illustrates flow cytometry graphs of the specificity assay of the AG13 DNA aptamer (SEQ ID NO:1) 620, the AG31 DNA aptamer (SEQ ID NO: 2) 622, and the library of DNA aptamers 618 against human hepatocellular carcinoma cell line (HepG2), consistent with one or more exemplary embodiments of the present disclosure.

Figure 6E:
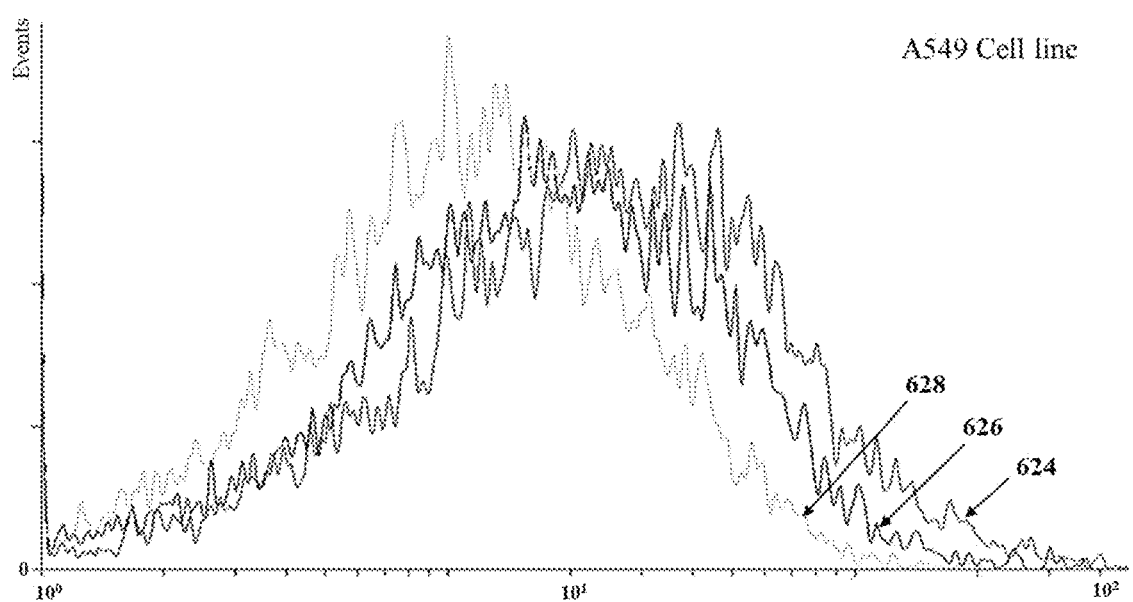
FIG. 6E illustrates flow cytometry graphs of the specificity assay of the AG13 DNA aptamer (SEQ ID NO:1), the AG31 DNA aptamer (SEQ ID NO: 2), and the library of DNA aptamers against human lung cancer cell line (A549), consistent with one or more exemplary embodiments of the present disclosure.
Figure 6F:
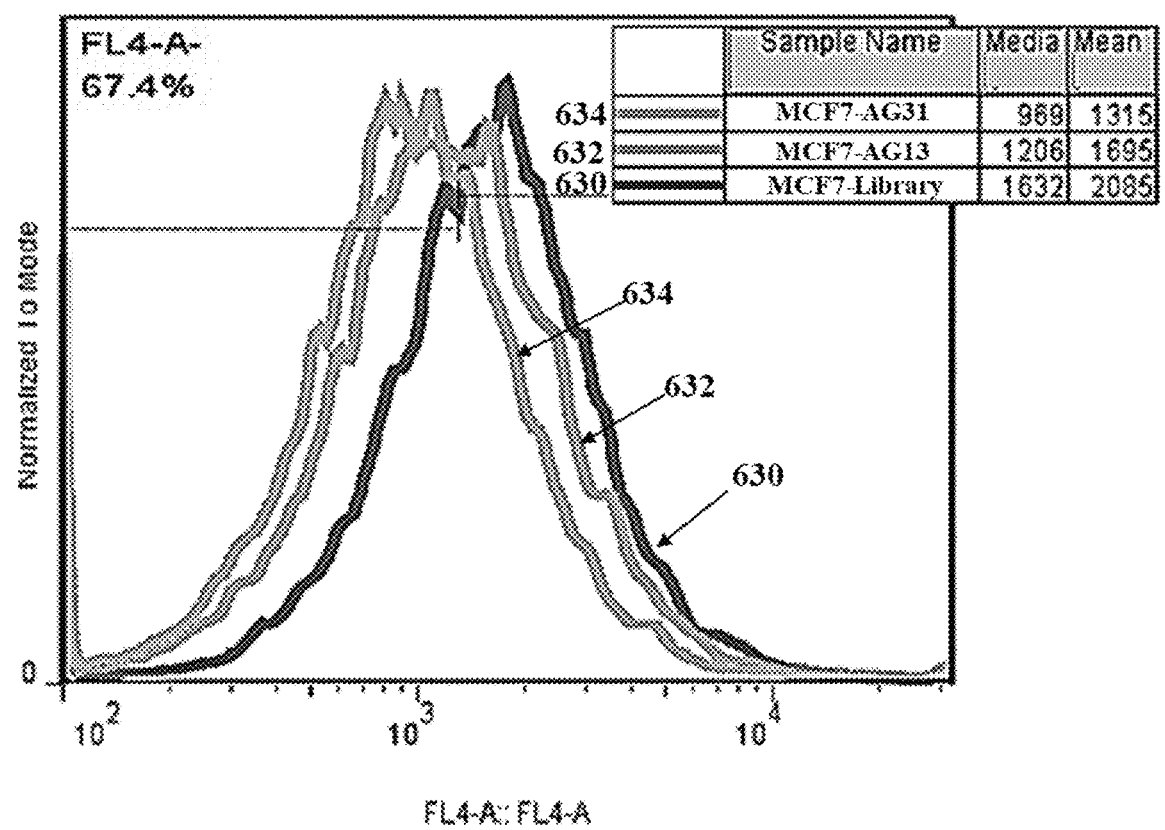
FIG. 6F illustrates flow cytometry graphs of the specificity assay of the AG13 DNA aptamer (SEQ ID NO:1), the AG31 DNA aptamer (SEQ ID NO: 2), and the library of DNA aptamers against human breast adenocarcinoma cell line (MCF-7), consistent with one or more exemplary embodiments of the present disclosure.

FIG. 6E illustrates flow cytometry graphs of the specificity assay of the AG13 DNA aptamer (SEQ ID NO:1) 626, the AG31 DNA aptamer (SEQ ID NO: 2) 628, and the library of DNA aptamers 624 against human lung cancer cell line (A549), consistent with one or more exemplary embodiments of the present disclosure. FIG. 6F illustrates flow cytometry graphs of the specificity assay of the AG13 DNA aptamer (SEQ ID NO:1) 632, the AG31 DNA aptamer (SEQ ID NO: 2) 634, and the library of DNA aptamers 630 against human breast adenocarcinoma cell line (MCF-7), consistent with one or more exemplary embodiments of the present disclosure.

Referring to FIGS. 6A-6F, the cells treated with the AG13 DNA aptamer (SEQ ID NO:1) and the AG31 DNA aptamer (SEQ ID NO: 2) had lower fluorescence intensities in comparison with the fluorescence intensity of the cells treated with the library of DNA aptamers; as a result, that the selected aptamers did not bind to other cell lines and did not have cross-reactivity to other normal and cancer cell lines including HeLa, HUVEC, EPG85-257P, HepG2, A549, and MCF-7.

Figure 6G:
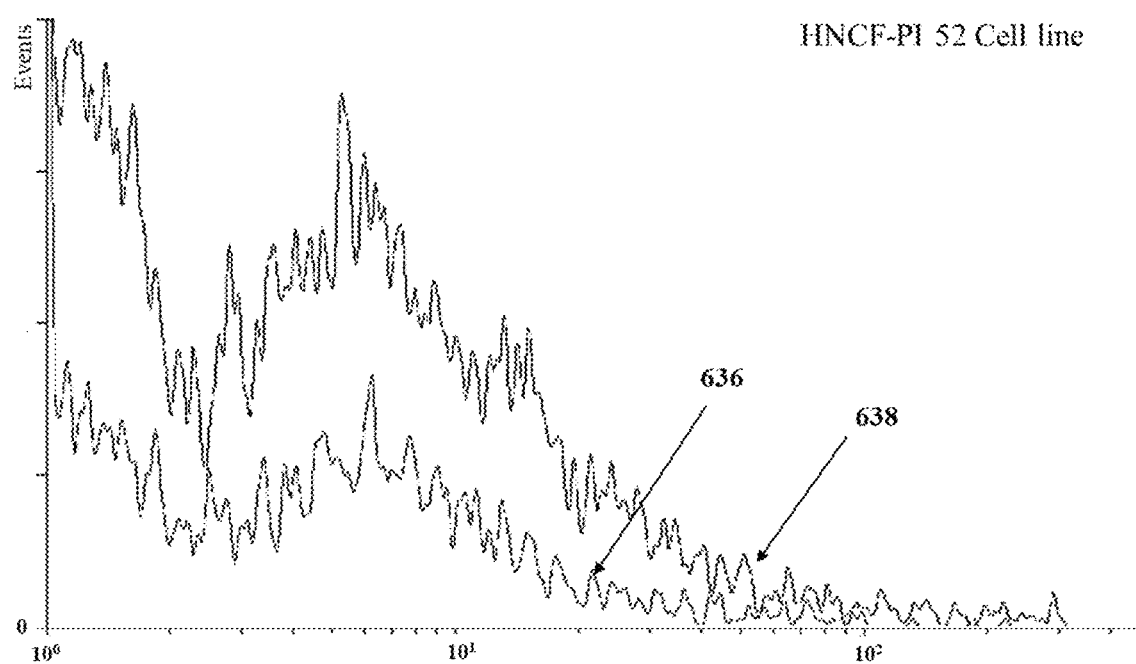
FIG. 6G illustrates flow cytometry graphs of the specificity assay of the AG31 DNA aptamer (SEQ ID NO: 2) and the library of DNA aptamers against human normal fibroblast-like cervical cell line (HNCF-PI 52), consistent with one or more exemplary embodiments of the present disclosure.

FIG. 6G illustrates flow cytometry graphs of the specificity assay of the AG31 DNA aptamer (SEQ ID NO: 2) 638 and the library of DNA aptamers 636 against HNCF-PI 52 cells, consistent with one or more exemplary embodiments of the present disclosure. Referring to FIG. 6G, the cells treated with the AG31 DNA aptamer (SEQ ID NO: 2) 638 showed higher fluorescence intensity in comparison with the cells treated with the library of DNA aptamers 636, which indicates that the AG31 DNA aptamer (SEQ ID NO: 2) was also capable of binding to HNCF-PI 52 cells. As a result, both of the CaSki cells as the target cells and the HNCF-PI 52 cells had target molecule of the AG31 DNA aptamer (SEQ ID NO: 2) on their surfaces. While HNCF-PI 52 cell line was also a HPV16-positive cell line, viral proteins of the HPV16 may be considered as the target molecule of the AG31 DNA aptamer (SEQ ID NO: 2).

Example 4: Internalization of Selected DNA Aptamers into HPV16-Positive Tumor Cells In this example, the internalization of the selected DNA aptamer into the CaSki (CRL1550) cells was assessed using flow cytometry analysis. The CaSki cells as the HPV16-positive tumor cells cultured in 24-well plates were treated with 100 nM of selected DNA aptamers labeled with ATTO 647N fluorescent labels. The CaSki cells treated with the selected DNA aptamers were incubated at temperatures of about 4° C. and about 37° C. for time periods of about 45 minutes and 2 hours.

Figure 7A:
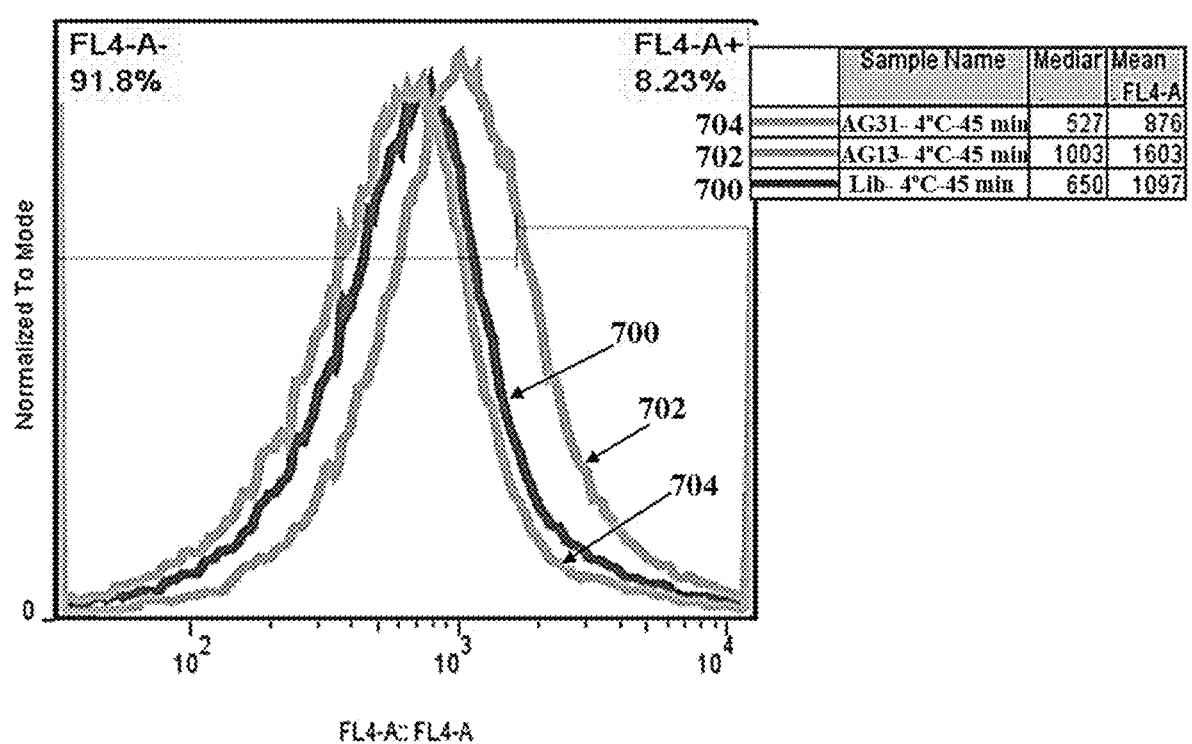
FIG. 7A illustrates flow cytometry graphs of the internalization assay of the AG13 DNA aptamer (SEQ ID NO: 1), the AG31 DNA aptamer (SEQ ID NO: 2), and the library of the DNA aptamer into the HPV16-positive tumor cells at a temperature of about 4° C. after about 45 minutes, consistent with one or more exemplary embodiments of the present disclosure.

FIG. 7A illustrates flow cytometry graphs of the internalization assay of the AG13 DNA aptamer (SEQ ID NO: 1) 702, the AG31 DNA aptamer (SEQ ID NO: 2) 704, and the library of the DNA aptamer 700 into the HPV16-positive tumor cells at a temperature of about 4° C. after about 45 minutes, consistent with one or more exemplary embodiments of the present disclosure.

Figure 7B:
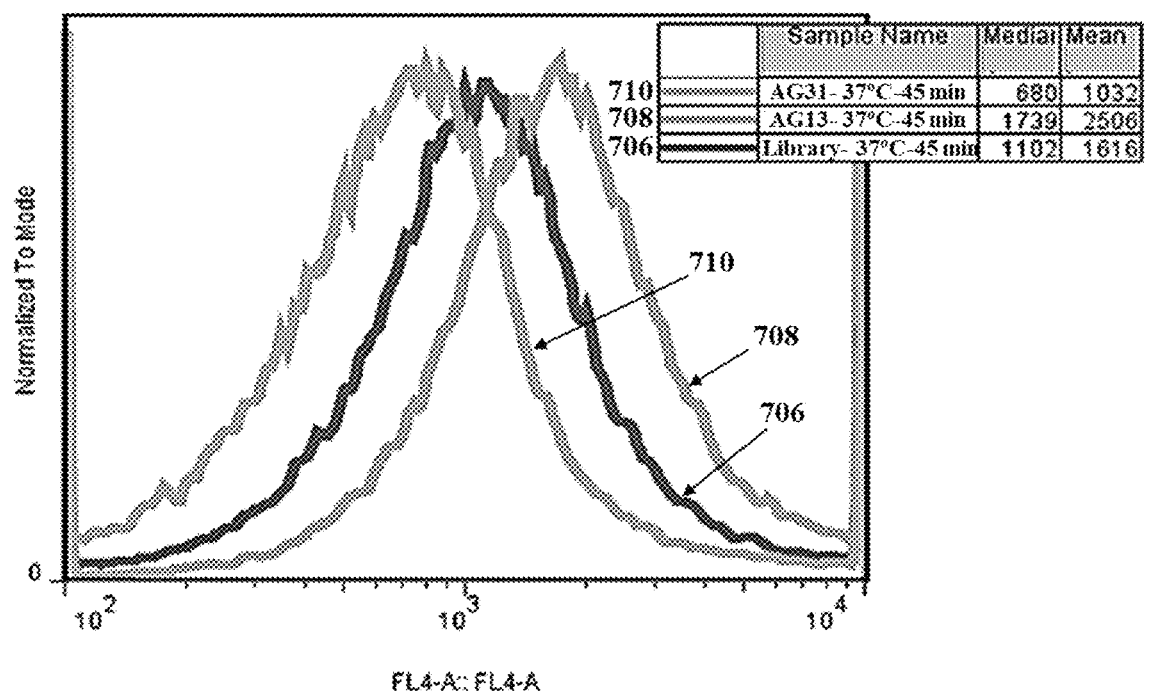
FIG. 7B illustrates flow cytometry graphs of the internalization assay of the AG13 DNA aptamer (SEQ ID NO: 1), the AG31 DNA aptamer (SEQ ID NO: 2), and the library of the DNA aptamer into the HPV16-positive tumor cells at a temperature of about 37° C. after about 45 minutes, consistent with one or more exemplary embodiments of the present disclosure.

FIG. 7B illustrates flow cytometry graphs of the internalization assay of the AG13 DNA aptamer (SEQ ID NO: 1) 708, the AG31 DNA aptamer (SEQ ID NO: 2) 710, and the library of the DNA aptamer 706 into the HPV16-positive tumor cells at a temperature of about 37° C. after about 45 minutes, consistent with one or more exemplary embodiments of the present disclosure.

Referring to FIGS. 7A-7B, the AG13 DNA aptamer (SEQ ID NO: 1) 708 at a temperature of about 37° C. had a 1.7-fold increase in fluorescence intensity compared to the fluorescence intensity of AG13 DNA aptamer (SEQ ID NO: 1) 702 at a temperature of about 4° C. The AG31 DNA aptamer (SEQ ID NO: 2) 704 at a temperature of about 37° C. has a 1.29-fold increase in the fluorescence intensity compared to the fluorescence intensity of the AG31 DNA aptamer (SEQ ID NO: 2) 710 at a temperature of about 4° C. The library of the DNA aptamer 706 shows a fluorescence intensity with a 1.69-fold increase compared to the library's fluorescence intensity of the DNA aptamer 700. The increase in the selected aptamers' fluorescence intensities was lower or almost the same as the increase in DNA aptamers' library. Therefore, the selected aptamers could not enter the CaSki cells.

Figure 8A:
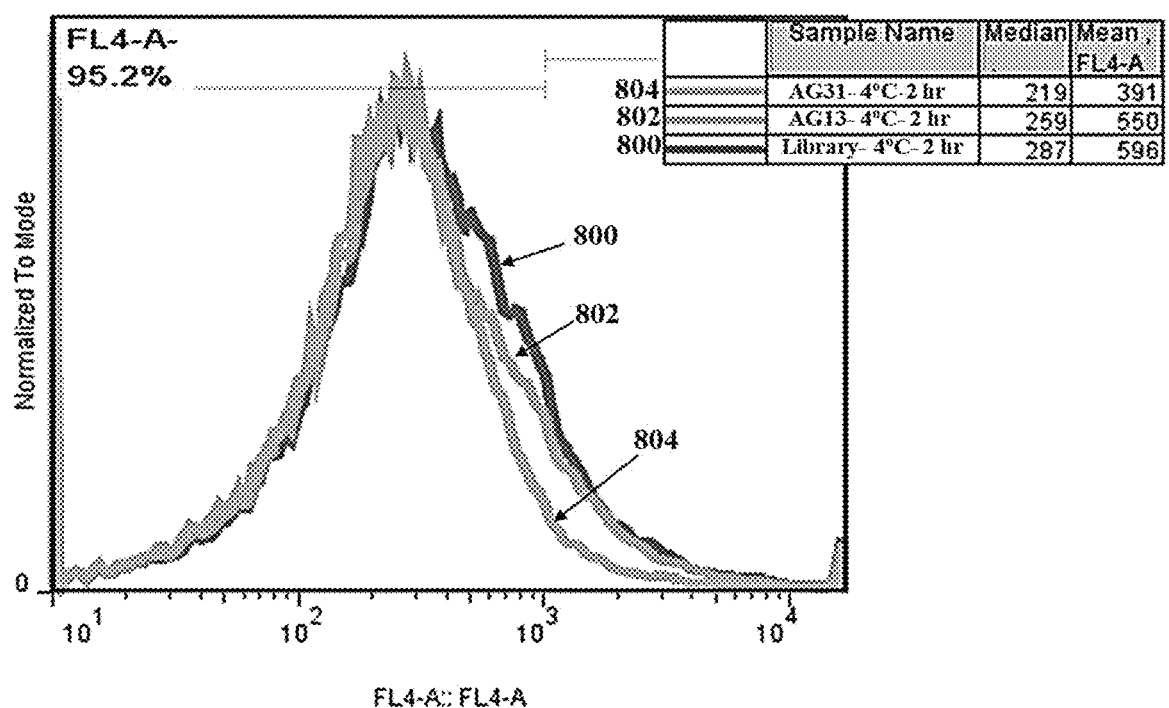
FIG. 8A illustrates flow cytometry graphs of the internalization assay of the AG13 DNA aptamer (SEQ ID NO: 1), the AG31 DNA aptamer (SEQ ID NO: 2), and the library of the DNA aptamer into the HPV16-positive tumor cells at a temperature of about 4° C. after two (2) hours, consistent with one or more exemplary embodiments of the present disclosure.

To further verify the internalization assay, the test was repeated by increasing the DNA aptamers' incubation time with the CaSki cells from 45 minutes to 2 hours. FIG. 8A illustrates flow cytometry graphs of the internalization assay of the AG13 DNA aptamer (SEQ ID NO: 1) 802, the AG31 DNA aptamer (SEQ ID NO: 2) 804, and the library of the DNA aptamer 800 into the HPV16-positive tumor cells at a temperature of about 4° C. after two (2) hours, consistent with one or more exemplary embodiments of the present disclosure.

Figure 8B:
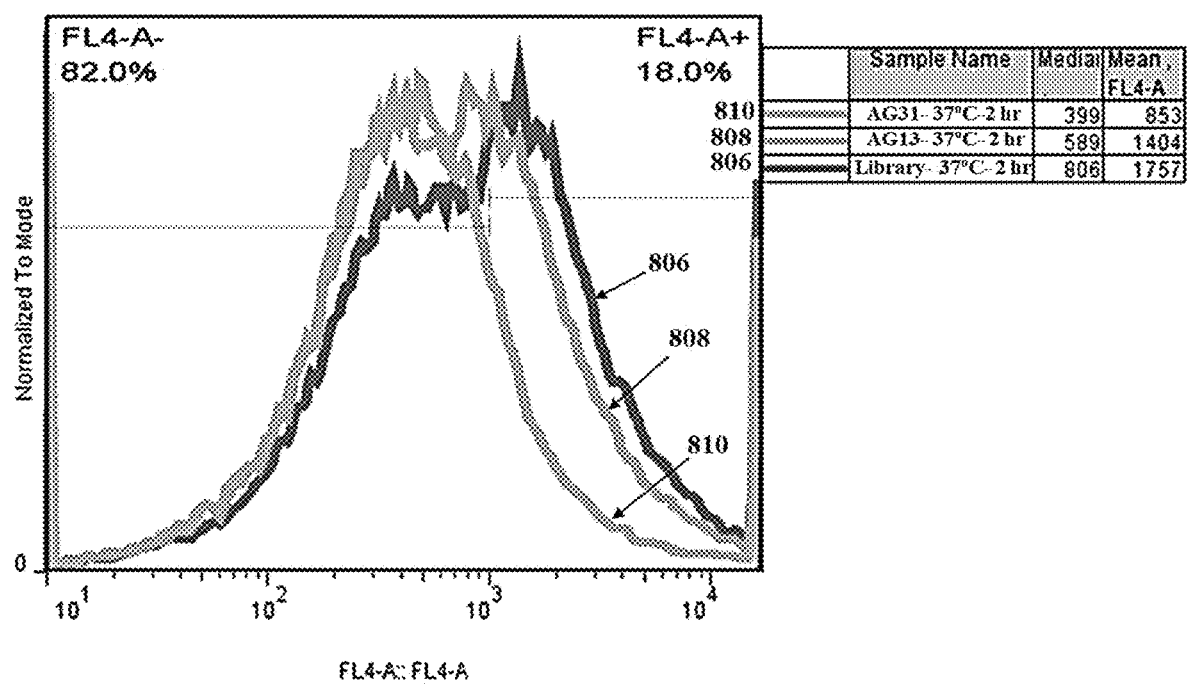
FIG. 8B illustrates flow cytometry graphs of the internalization assay of the AG13 DNA aptamer (SEQ ID NO: 1), the AG31 DNA aptamer (SEQ ID NO: 2), and the library of the DNA aptamer into the HPV16-positive tumor cells at a temperature of about 37° C. after two (2) hours, consistent with one or more exemplary embodiments of the present disclosure.

FIG. 8B illustrates flow cytometry graphs of the internalization assay of the AG13 DNA aptamer (SEQ ID NO: 1) 808, the AG31 DNA aptamer (SEQ ID NO: 2) 810, and the library of the DNA aptamer 806 into the HPV16-positive tumor cells at a temperature of about 37° C. after two (2) hours, consistent with one or more exemplary embodiments of the present disclosure.

Referring to FIGS. 8A-8B, the fluorescence intensity of the library of DNA aptamer 806 at a temperature of about 37° C. showed a 2.8-fold increase compared to the library of DNA aptamer 800 at a temperature of about 4° C. However, the selected DNA aptamers of AG13 (SEQ ID NO: 1) 808 and AG31 (SEQ ID NO: 2) 810 showed a lower increase in fluorescence intensities compared to the library of DNA aptamers (2.27-fold increase for AG13 DNA aptamer and 1.82-fold increase for AG31 DNA aptamer compared to related fluorescence intensities 802 and 804 at a temperature of about 4° C.). As a result, the internalization assays results show that none of the AG13 DNA aptamer (SEQ ID NO: 1) and the AG31 DNA aptamer (SEQ ID NO: 2) could enter the CaSki cells as their target cells.

Example 5: Target Molecules of Selected DNA Aptamers on the HPV16-Positive Tumor Cells In this example, the selected DNA aptamer's target molecules, including AG13 (SEQ ID NO: 1) and AG31 (SEQ ID NO: 2) on a surface of the CaSki (CRL1550) cells as the HPV16-positive tumor cells were verified as membrane proteins through conducting a proteinase digestion experiment. At first, the CaSki cells were cultured in 24-well plates for a time period of about 48 hours. Then, the selected DNA aptamer and the library of DNA aptamers were added to the cultured cells with an amount of about 100 nM for each well. After adding the DNA aptamers to the cells, the cultured cells were washed twice with the DPBS to remove the aptamers' excess amount.

In the next step, the cells were treated with a proteinase in different conditions, including treating with 200 µl of 0.05% trypsin at 37° C. for 3 minutes and 10 minutes in separate wells and treating with both trypsin and 0.2 mg/µl proteinase K at 37° C. for 10 minutes. The reaction was terminated by adding a complete medium. The cells of each well were detached by a scraper and applied for the flow cytometry assay. Also, the CaSki cells without aptamer were treated with trypsin and proteinase K for a time period of about 3 minutes and 10 minutes using a flow cytometer as a negative control.

Figure 9A:
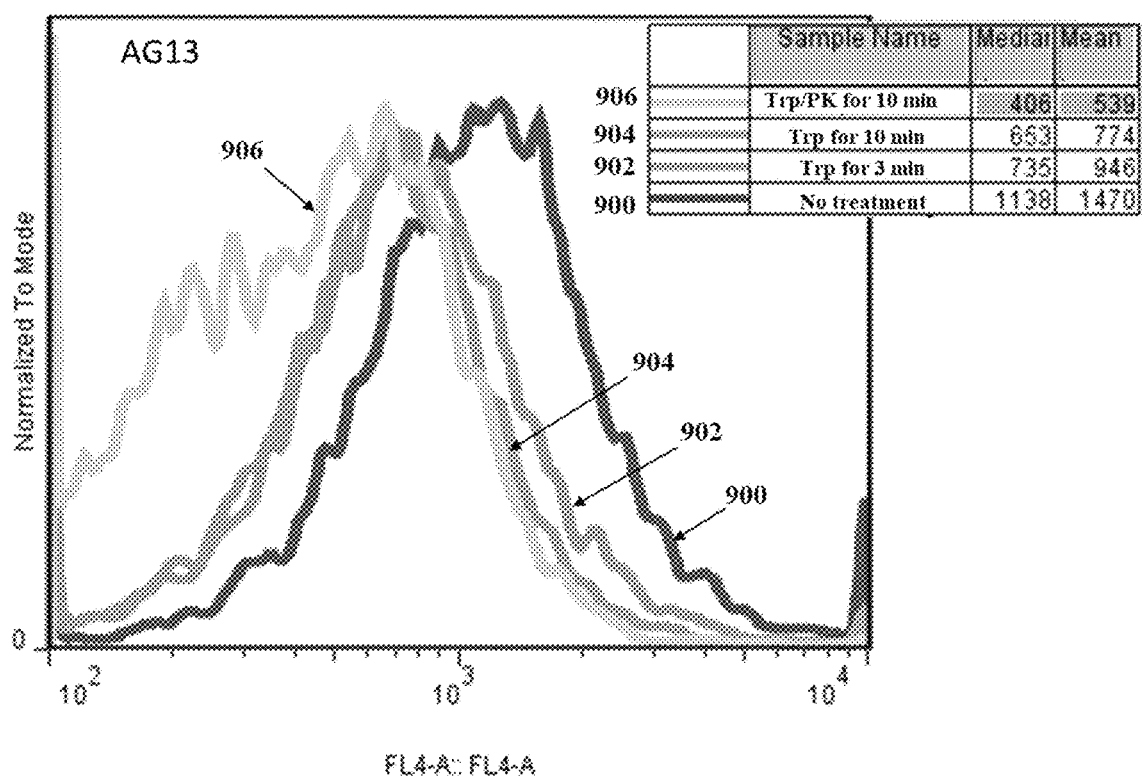
FIG. 9A illustrates flow cytometry graphs of binding of the AG13 DNA aptamer (SEQ ID NO: 1) to CaSki (CRL1550) cells as HPV16-positive tumor cells with different treatments, including no protease treatment, treatment with trypsin for 3 minutes, treatment with trypsin for 10 minutes, and treatment with trypsin/proteinase K for 10 minutes, consistent with one or more exemplary embodiments of the present disclosure.
Figure 9B:
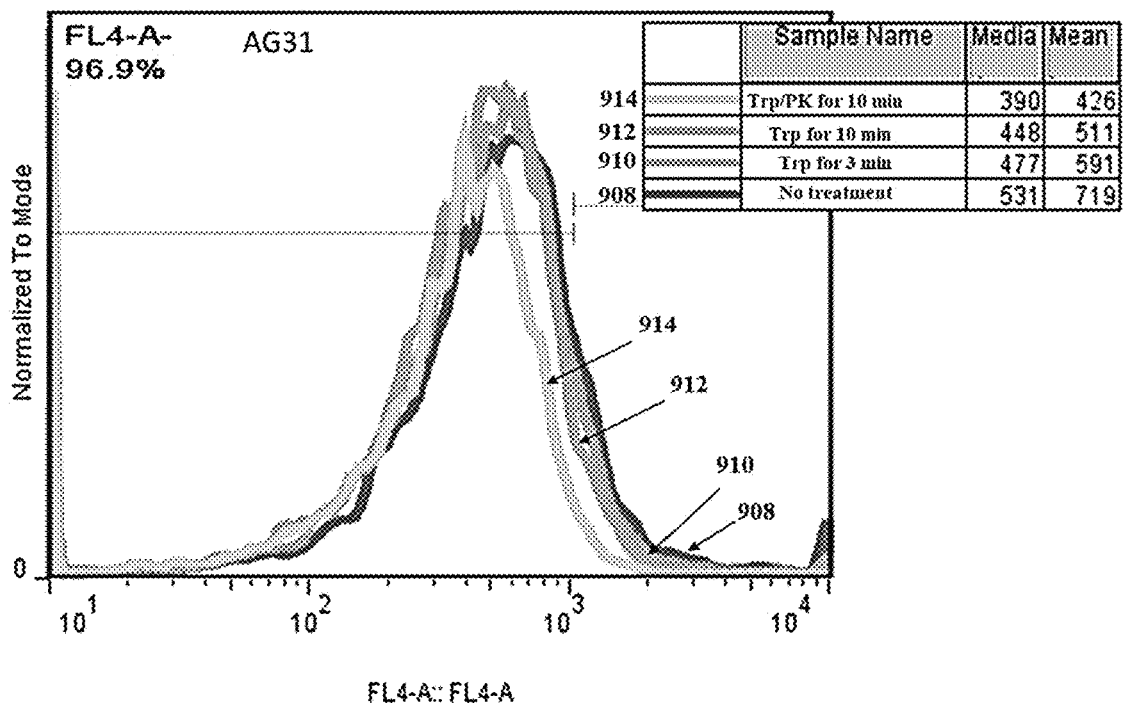
FIG. 9B illustrates flow cytometry graphs of binding of the AG31 DNA aptamer (SEQ ID NO: 2) to CaSki cells as HPV16-positive tumor cells with different treatments, including no protease treatment, treatment with trypsin for 3 minutes, treatment with trypsin for 10 minutes, and treatment with trypsin/proteinase K for 10 minutes, consistent with one or more exemplary embodiments of the present disclosure.

FIG. 9A illustrates flow cytometry graphs of binding of the AG13 DNA aptamer (SEQ ID NO: 1) to CaSki cells as HPV16-positive tumor cells with different treatments including no proteinase treatment 900, treatment with trypsin for 3 minutes 902, treatment with trypsin for 10 minutes 904, and treatment with trypsin/proteinase K for 10 minutes 906, consistent with one or more exemplary embodiments of the present disclosure. FIG. 9B illustrates flow cytometry graphs of binding of the AG31 DNA aptamer (SEQ ID NO: 2) to CaSki cells as HPV16-positive tumor cells with different treatments including no proteinase treatment 908, treatment with trypsin for 3 minutes 910, treatment with trypsin for 10 minutes 912, and treatment with trypsin/proteinase K for 10 minutes 914, consistent with one or more exemplary embodiments of the present disclosure.

Referring to FIGS. 9A-9B, the treated CaSki cells of all treatments 902, 904, 906, 910, 912, and 914 showed a lower fluorescence intensity in comparison with the CaSki cells with no proteinase treatment 900 and 908; as a result, the treated CaSki cells almost did not bind to the AG13 DNA aptamer and the AG31 DNA aptamer, indicating that the target molecules of the AG13 DNA aptamer (SEQ ID NO: 1) and the AG31 DNA aptamer (SEQ ID NO: 2) were membrane proteins which degraded during the proteinase digestion experiment.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such away. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A composition for binding to human papillomavirus type 16 (HPV16)-positive tumor cells, the composition comprising a DNA aptamer, the DNA aptamer comprising one of SEQ ID NO: 1 and SEQ ID NO: 2.

2. The composition of claim 1, wherein the DNA aptamer has a dissociation constant ($K_d$) between 10 nM and 190 nM.

3. The composition of claim 1, wherein the HPV16-positive tumor cells comprises at least one of HPV16-positive cervical cancer cells, HPV16-positive head and neck cancer cells, HPV16-positive oropharynx cancer cells, HPV16-positive anal cancer cells, HPV16-positive vaginal cancer cells, HPV16-positive penile cancer cells, HPV16-positive vulvar cancer cells, HPV16-positive breast cancer cells, and HPV16-positive gastrointestinal cancer cells.

4. The composition of claim 1 further comprising a tag conjugated to the DNA aptamer, the tag comprising at least one of a therapeutic tag and a diagnostic tag.

5. The composition of claim 4, wherein the diagnostic tag comprises at least one of a radioactive substance, a dye, a contrast agent, a fluorophore molecule, a nanoparticle, a bioluminescent molecule, affinity agent, and a magnetic agent.

6. The composition of claim 5, wherein the radioactive substance comprises at least one of phosphorus-32 ($^{32}P$), sulfur-35 ($^{35}S$), and phosphorus-33 ($^{33}P$).

7. The composition of claim 5, wherein the dye comprises at least one of a cyanine dye and methylene blue.

8. The composition of claim 5, wherein the contrast agent comprises at least one of gadolinium nanoparticles and superparamagnetic iron oxide nanoparticles.

9. The composition of claim 5, wherein the fluorophore molecule comprises at least one of acridine orange, auramine, crystal violet, malachite green, porphin, phthalocyanine, cresyl violet, fluorescein, rhodamine, green fluorescent dye, eosin, cyanine derivatives, blue fluorescent DNA dye, a green fluorescent protein (GFP), and 4',6-diamidino-2-phenylindole (DAPI).

10. The composition of claim 5, wherein the nanoparticle comprises at least one of superparamagnetic nanoparticles, gold nanoparticles, carbon nanotubes, silica nanoparticles, metal nanoparticles, graphene oxide nanoparticles, and metal-organic frameworks.

11. The composition of claim 5, wherein the bioluminescent molecule comprises luciferase.

12. The composition of claim 5, wherein the magnetic agent comprises a magnetic bead.

13. The composition of claim 5, wherein the affinity tag comprises at least one of a streptavidin/biotin-based tag, a polyhistidine tag, and maltose-binding protein (MBP) tag.

14. The composition of claim 4, wherein the therapeutic tag comprises at least one of a chemotherapeutic drug, a toxin, an anti-cancer growth inhibitor compound, an anti-cancer siRNA, and an anti-cancer antagomir.

15. The composition of claim 14, wherein the chemotherapeutic drug comprises at least one of cisplatin, paclitaxel, carboplatin, topotecan, 5-fluorouracil, mitomycin C, docetaxel, oxaliplatin, epirubicin, cyclophosphamide, methotrexate, doxorubicin, and irinotecan.

16. A method for detecting human papillomavirus type 16 (HPV16)-positive tumor cells in a biological sample, the method comprising:

putting the biological sample in contact with a composition, the composition comprising:

a DNA aptamer comprising one of SEQ ID NO: 1 and SEQ ID NO: 2; and a diagnostic tag conjugated to the DNA aptamer; and determining the presence of an HPV16-positive tumor cell in the biological sample responsive to detecting the DNA aptamer bound to the HPV16-positive tumor cell.

17. The method of claim 16, wherein detecting the DNA aptamer bound to the HPV16-positive tumor cell comprises detecting a signal generated by the diagnostic tag responsive to binding the DNA aptamer to the HPV16-positive tumor cells by conducting at least one of a chemiluminescent assay, a fluorescent assay, enzyme-linked apta-sorbent assay (ELASA), radioimmunoassay, a Western blot assay, an apta-precipitation assay, an apta-histochemical assay, an immunochromatographic assay, a dot blot assay, a slot blot assay, confocal imaging, laser scanning microscopy, and flow cytometry.

18. The method of claim 16, wherein putting the biological sample in contact with the composition comprises putting at least one of a blood sample, a plasma sample, a serum sample, a urine sample, a fecal sample, a cervix sample, and a semen sample in contact with the composition.

19. A method for targeting human papillomavirus type 16 (HPV16)-positive tumor cells in a subject, the method comprising administering a composition to the subject, the composition comprising:

a DNA aptamer comprising one of SEQ ID NO: 1 and SEQ ID NO: 2; and a tag conjugated to the DNA aptamer, the tag comprising at least one of a diagnostic tag and a therapeutic tag.

20. The method of claim 19 further comprising killing the HPV16-positive tumor cells in the subject by conducting at least one of magnetic hyperthermia, photodynamic therapy, and photothermal therapy.

* * * * *